(12) United States Patent
Chouinard et al.

(10) Patent No.: US 11,197,750 B2
(45) Date of Patent: Dec. 14, 2021

(54) EMBOLIC PROTECTION DEVICE

(71) Applicant: Lake Region Manufacturing, Inc., Chaska, MN (US)

(72) Inventors: Brian Chouinard, Peabody, MA (US); David Keary, Galway (IE); Aran Murray, Galway (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 241 days.

(21) Appl. No.: 15/825,528

(22) Filed: Nov. 29, 2017

(65) Prior Publication Data
US 2018/0147041 A1 May 31, 2018

Related U.S. Application Data

(60) Provisional application No. 62/427,247, filed on Nov. 29, 2016.

(51) Int. Cl.
*A61F 2/01* (2006.01)
*A61M 25/10* (2013.01)

(52) U.S. Cl.
CPC ........ *A61F 2/013* (2013.01); *A61M 25/104* (2013.01); *A61F 2002/015* (2013.01); *A61F 2002/016* (2013.01); *A61F 2230/0004* (2013.01); *A61F 2230/0067* (2013.01)

(58) Field of Classification Search
CPC ...... A61F 2/01; A61F 2/013; A61F 2002/011; A61F 2002/015; A61F 2002/016; A61F 2002/018; A61F 2/0103; A61F 2/0105; A61F 2/0108; A61F 2230/004; A61F 2230/0067; A61M 25/104

USPC ...................................................... 606/200
See application file for complete search history.

(56) References Cited

U.S. PATENT DOCUMENTS

| | | | |
|---|---|---|---|
| 4,795,458 A | 1/1989 | Regan | |
| 5,037,427 A | 8/1991 | Harada et al. | |
| 5,089,005 A | 2/1992 | Harada et al. | |
| 5,466,242 A | 11/1995 | Mori | |
| 5,769,816 A | 6/1998 | Barbut et al. | |
| 6,139,517 A | 10/2000 | Macoviak et al. | |
| 6,245,012 B1 * | 6/2001 | Kleshinski | A61F 2/011 623/1.11 |

(Continued)

FOREIGN PATENT DOCUMENTS

WO     2004019817     3/2004

OTHER PUBLICATIONS

Webster's New World College Dictionary, Fifth Ed., Imperforate Definition, (2014) Houghton Mifflin Harcourt Publishing Co., accessed, https://www.yourdictionary.com/impeforate on Aug. 27, 2020 (Year: 2014).*

(Continued)

*Primary Examiner* — Wade Miles
*Assistant Examiner* — Kankindi Rwego
(74) *Attorney, Agent, or Firm* — Michael F. Scalise

(57) ABSTRACT

Disclosed herein are devices and methods for providing embolic protection in a patient's vascular system. In particular, the devices detailed herein are supported by a flexible scaffold that is coupled to a filter. When deployed into the peripheral or coronary vasculature of a patient, the embolic protection devices of the present disclosure collect and remove embolic debris as a prophylactic measure to lessen the risk of embolic associated complications.

34 Claims, 7 Drawing Sheets

(56) References Cited

U.S. PATENT DOCUMENTS

| | | |
|---|---|---|
| 6,254,563 B1 | 7/2001 | Macoviak et al. |
| 6,361,545 B1 | 3/2002 | Macoviak et al. |
| 6,371,935 B1 | 4/2002 | Macoviak et al. |
| 6,499,487 B1 | 12/2002 | McKenzie et al. |
| 6,537,297 B2 | 3/2003 | Tsugita et al. |
| 8,070,769 B2 | 12/2011 | Broome et al. |
| 9,198,687 B2 * | 12/2015 | Fulkerson ............ A61B 17/221 |
| 2002/0042627 A1 | 4/2002 | Brady et al. |
| 2003/0023265 A1* | 1/2003 | Forber .................... A61F 2/013 606/200 |
| 2003/0042186 A1* | 3/2003 | Boyle ..................... A61F 2/013 210/136 |
| 2003/0100917 A1* | 5/2003 | Boyle .................... B82Y 30/00 606/200 |
| 2003/0100940 A1 | 5/2003 | Yodfat et al. |
| 2004/0082967 A1* | 4/2004 | Broome ................. A61F 2/013 606/200 |
| 2004/0215167 A1 | 10/2004 | Belson et al. |
| 2005/0177186 A1* | 8/2005 | Cully .............. A61B 17/12109 606/200 |
| 2017/0049552 A1* | 2/2017 | Inoue ..................... A61B 17/00 |
| 2017/0112513 A1* | 4/2017 | Marchand ............ A61B 17/221 |
| 2017/0312069 A1 | 11/2017 | Sachar et al. |

OTHER PUBLICATIONS

"Heart and Stroke Statistics", American Heart Association website; High Blood Pressure Guidelines.

Charles, et al., "Diagnosis of Coronary Embolism: A Review", Journal of the Royal Society of Medicine vol. 76, Oct. 1983, pp. 863 to 869.

Falk, et al., "Pathology of Coronary Microembolisation and no Reflow", Heart Journal, Mini-Symposium, 2003; 89: pp. 983-985.

Goldsmith, et al., "Regional Cerebral Blood Flow After Omental Transposition to the Ischaemic Brain in Man. A Five Year Follow-Up Study", Acta Neurochir (Wien)(1990) 106: pp. 145-152.

Sangiorgi, et al., "Embolic Protection Devices", Mini-Symposium, Heart Journal 2003, 89: 990-992.

Tapson, "Acute Pulmonary Embolism", The New England Journal of Medicine, Medical Progress, 2008; 358: 1037-1052.

* cited by examiner

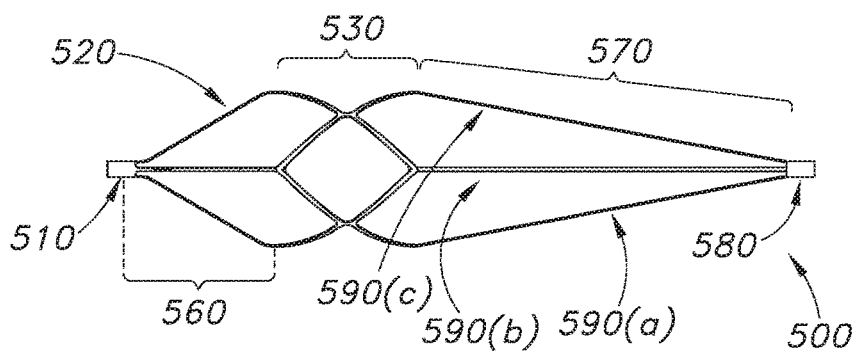
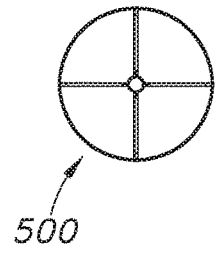
FIG. 5A
FIG. 5B
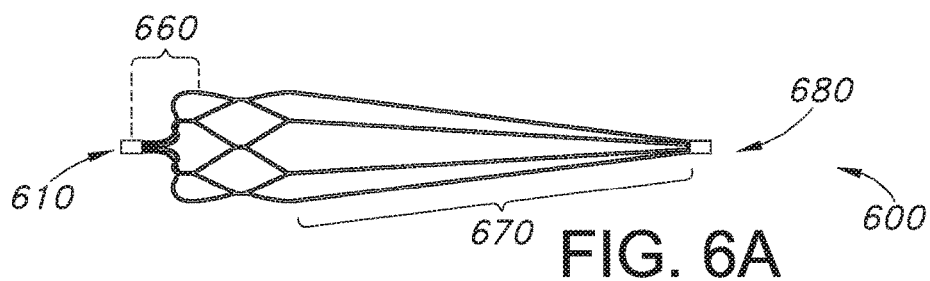
FIG. 6A
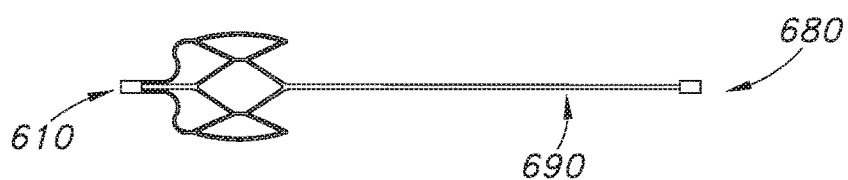
FIG. 6B
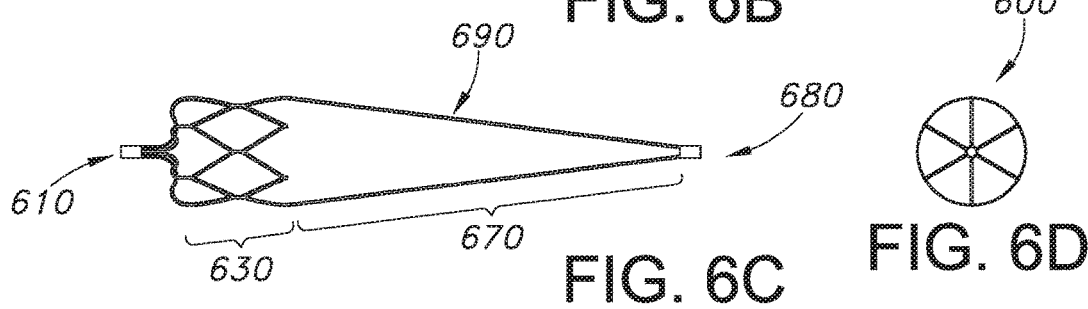
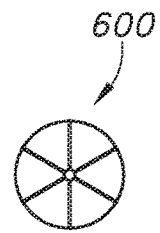
FIG. 6C
FIG. 6D

EMBOLIC PROTECTION DEVICE

CROSS-REFERENCE TO RELATED APPLICATIONS

This application claims priority to U.S. Provisional Patent Application Ser. No. 62/427,247 "Embolic Protection Devices Having Laser Cut Frames," which was filed on Nov. 29, 2016, the entire contents of which are hereby incorporated by reference in its entirety.

FIELD OF THE INVENTION

The present disclosure relates generally to apparatuses and methods for providing embolic protection. In particular, the present disclosure relates to the collection and removal of emboli in the peripheral and coronary vasculature of a patient in need thereof.

BACKGROUND OF THE INVENTION

The following description is provided to assist the understanding of the reader. None of the information provided or references cited is admitted to be prior art.

An embolism can be generally defined as a blood vessel obstruction due to a blood clot or other occlusion that has materialized as a static deposit within the peripheral or coronary vasculature of an individual. Embolic particles or debris, such as thrombus, atheroma, and lipids, moreover, are embolism precursors and accordingly the etiological agents of various medical conditions, including stroke, pulmonary and myocardial infarction, and kidney failure. See, e.g., Tapson, V. "Acute Pulmonary Embolism" *N. Engl. J. Med.,* 358: 1037-52 (2008); see also Charles and Epstein, "Diagnosis of Coronary Embolism: a review," *J. R. Soc. Med.,* 76(10): 863-9 (1983). To this end, embolic prophylaxis or protection is a clinical model directed at reducing the risk of embolic complications associated with various interventional procedures.

With respect to therapeutic vascular procedures, the liberation of embolic debris, such as, e.g., thrombus, clots, and atheromatous plaque, can obstruct perfusion of downstream vasculature, which may result in deleterious ischemic conditions for a patient. Vascular procedures most commonly associated with adverse embolic complications include, for example, carotid angioplasty and revascularization of degenerated saphenous vein grafts. Additionally, percutaneous transluminal coronary angioplasty, surgical coronary artery bypass grafting, percutaneous renal artery revascularization, endovascular aortic aneurysm repair, cardiopulmonary bypass, peripheral vascular surgeries, electrophysiological procedures, and catheter-based interventional cardiology, are similarly associated with complications attributable to embolization.

As a manifest complication of cardiopulmonary procedures, embolic debris borne out of such surgical interventions impart a substantial risk to the patient insofar as the potential for surgical dislodgment and dissemination portend the vascular redistribution of such particles, which can be fatal, i.e., when embolizing to the brain or other vital organs. Emboli also emanate from ruptured or vulnerable plaque, which is typically the case for cardiogenic emboli, e.g., thrombus, that result from chronic atrial fibrillation in many instances. If not fatal, downstream vascular systems are nonetheless confronted with the damaging impact of vasculature stasis or ischemia, which can lead to diminished organ function and quality of life for the patient. The use of embolic protection devices to capture and remove embolic detritus, in this regard, consequently imparts a rubric for improving patient outcomes via curtailing the incidence of embolic complications at its origin, i.e., by capturing embolic debris before a downstream occlusion precipitates.

SUMMARY

In one aspect, the present disclosure is directed to an embolic protection device that entails a conical filter including perforations for fluid flow therethrough, and a proximally located ingress, and a scaffold that entails a proximal eyelet having an eyelet axis extending therethrough, where the proximal eyelet defines a proximal scaffold end, and an elastomeric frame adapted to operate between expanded and collapsed profiles, where the frame includes struts extending from the proximal eyelet to define a proximal strut region, and a frame-cell region having a first edge that is continuous with the proximal strut region, where the filter is coupled to at least a portion of the frame-cell region to form the embolic protection device. In some embodiments, the embolic protection device further entails an insertable guide extending through the proximal eyelet and the elastomeric frame, where the insertable guide facilitates deployment and directional positioning of the device along the eyelet axis.

In illustrative embodiments, the scaffold further comprises a distal eyelet oriented about the eyelet axis and defines a distal scaffold end, and where distal struts extend from the distal scaffold end to define a distal strut region that is continuous with a second edge of the frame-cell region. In some embodiments, the elastomeric frame is composed of a material selected from nitinol, stainless steel, titanium, and alloys thereof, and combinations thereof. In certain embodiments, the struts are radially oriented relative to the eyelet axis, and extend from the proximal eyelet at an angle ranging from about 10° to about 90° relative to the eyelet axis.

The conical filter has a polymeric material selected from one or more fluoropolymers, polytetrafluoroethylene (PTFE), ePTFE, polyurethane, and polyethylene, and combinations thereof, in certain embodiments. In illustrative embodiments, the perforations possess a pore diameter of about 5 µm to about 200 µm, while in some embodiments, the filter further entails an imperforated section configured to circumferentially conform to an interior segment of the frame-cell region. In illustrative embodiments, the imperforated section is composed of alternating embrasure segments each separated by an abapical region disposed about the eyelet axis to define a coupling configuration.

In illustrative embodiments, at least one of the abapical regions is occupied by the imperforated filter material to define an off-set coupling configuration. The conical filter, moreover, is bonded to the portion of the frame-cell region, in suitable embodiments. In some embodiments, an attachment couples the conical filter to an interior segment of the frame-cell region. The distal strut region is tapered towards the distal eyelet along the eyelet axis, in some embodiments, and has a length of about 1.5 to about 10 times that of either or both of the proximal strut region and the frame-cell region.

The conical filter is disposed internal to the scaffold and tapers distally along the eyelet axis, in some embodiments. Likewise, in certain embodiments, the conical filter is disposed internal to the scaffold and tapers distally along the eyelet axis. In some embodiments, the frame-cell region comprises a strut matrix circumferentially disposed about the eyelet axis. In illustrative embodiments, the scaffold is radially ridged to maintain blood vessel apposition in a deployed state. In some embodiments, the elastomeric frame comprises three integral struts.

In one aspect, the present disclosure provides an embolic protection system that entails a distally tapered filter that includes perforations for fluid flow therethrough, and an imperforated section that defines an ingress, while an integral scaffold includes a proximal eyelet defining a proximal end of the scaffold, a distal eyelet defining a distal end of the scaffold, where both of the eyelets are oriented about a longitudinal eyelet axis, and an elastomeric frame disposed between the proximal and distal eyelets, where the frame has proximal and distal struts extending from their respective eyelets to respectively define proximal and distal strut regions, and a frame-cell region disposed between, and continuous with, the proximal and distal strut regions, where the imperforated section of the filter is coupled to at least a portion of the frame-cell region, where the filter is disposed internal to the scaffold, and an insertable guide extending through the elastomeric frame and each of the eyelets to facilitate deployment and directional positioning of the embolic protection device along the eyelet axis.

In illustrative embodiments, the elastomeric frame is composed of a material selected from nitinol, stainless steel, titanium, and alloys thereof, and combinations thereof. In some embodiments, the struts are radially oriented relative to the eyelet axis, and extend from their respective eyelets at an angle ranging from about 10° to about 90° relative to the eyelet axis. In illustrative embodiments, the filter is composed of a polymeric material selected from one or more fluoropolymers, polytetrafluoroethylene (PTFE), ePTFE, polyurethane, and polyethylene, and combinations thereof.

The embolic protections systems of the present disclosure, in illustrative embodiments, possess perforations having a pore diameter of about 5 µm to about 200 µm. In certain embodiments, the imperforated section is composed of alternating embrasure segments each separated by an abapical region disposed about the eyelet axis to define a coupling configuration. In suitable embodiments, at least one of the abapical regions is occupied by the imperforated filter material to define an off-set coupling configuration. In illustrative embodiments, an attachment couples the imperforated section to the portion of the frame-cell region.

In illustrative embodiments, the distal strut region is tapered towards the distal eyelet along the eyelet axis, and has a length of about 1.5 to about 10 times that of either or both of the proximal strut region and the frame-cell region. The frame-cell region entails a strut matrix circumferentially disposed about the eyelet axis in certain embodiments. In some embodiments, the scaffold is radially ridged to maintain blood vessel apposition in a deployed state. In illustrative embodiments, the elastomeric frame comprises three integral struts.

In one aspect, the present disclosure entails a method of preventing a disease or condition associated with the presence of an embolism in a subject in need thereof, the method entailing (a) selected a subject, (b) accessing one or more blood vessels of the subject, (c) deploying an insertable guide, where the insertable guide is unilaterally or bilaterally positioned, (d) deploying an embolic protection device over the insertable guide, where steps (c) and (d) are performed separately, sequentially or simultaneously, and where the embolic protection device includes (i) a conical filter having perforations for fluid flow therethrough, and an imperforated section that defines an ingress, (ii) an integral scaffold having a proximal eyelet defining a proximal end of the scaffold, and a distal eyelet defining a distal end of the scaffold, and where both of the eyelets are oriented about a longitudinal eyelet axis.

In accord, the methods further entail (iii) an elastomeric frame disposed between the proximal and distal eyelets, with respect to the embolic protection device employed according to the methods of the present invention, where the elastomeric frame has proximal and distal struts extending from their respective eyelets to respectively define proximal and distal strut regions, a frame-cell region disposed between, and continuous with, the proximal and distal strut regions, and where the imperforated section is coupled to at least a portion of the frame-cell region, (iv) where the insertable guide extends through the elastomeric frame and each of the eyelets along the eyelet axis, (f) capturing embolic debris, and (g) removing the embolic protection device with the captured debris from the subject's blood vessel to prevent the disease or condition associated with the embolism in the subject.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIG. 1A is an isometric view of a single-eyelet, three-strut frame, scaffold. FIG. 1B is a rotational-isometric view of a single-eyelet, three-strut frame, scaffold. FIG. 1C is a longitudinal view of a single-eyelet, three-strut frame, scaffold. FIG. 1D is a perspective-isometric view of a single-eyelet, three-strut frame scaffold of the present invention.

FIG. 2A is an isometric view of a single-eyelet, four-strut frame, scaffold. FIG. 2B is a longitudinal view of a single-eyelet, four-strut frame, scaffold. FIG. 2C is a perspective-isometric view of a single-eyelet, four-strut frame scaffold of the present invention.

FIG. 3A is a flat-isometric view of a dual eyelet, three-strut frame, scaffold, of the present invention. FIG. 3B is a rotated flat-isometric view of a dual eyelet, three-strut frame, scaffold, of the present invention. FIG. 3C shows an orthogonal end-view configuration of the present invention with eyelets and struts depicted.

FIG. 4A is a flat-isometric view of a dual eyelet, inverted three-strut frame, scaffold of the present invention. FIG. 4B is a rotated flat-isometric view of a dual eyelet, inverted three-strut frame, scaffold, of the present invention. FIG. 4C shows an orthogonal end-view configuration of the present invention with eyelets and struts depicted.

FIGS. 5A-5B show perspective-isometric views of an illustrative representation of the present invention. FIG. 5A is a perspective-isometric view of a dual eyelet, four-strut frame, scaffold of the present invention. FIG. 5B is a longitudinal view of a dual eyelet, four-strut frame, scaffold of the present invention.

FIGS. 6A-6D show perspective-isometric views of an illustrative representation of the present invention. FIG. 6A is a perspective-isometric view of a dual eyelet, inverted six-strut frame, scaffold of the present invention. FIG. 6B is a perspective isometric view of a dual eyelet, inverted proximal six-strut and distal two-strut frame, scaffold of the present invention. FIG. 6C is a rotational isometric view of a dual eyelet, inverted proximal six-strut and distal two-strut frame, scaffold of the present invention. FIG. 6D is a longitudinal view of a dual eyelet, inverted six-strut frame, scaffold of the present invention.

FIG. 7A is a perspective-isometric view of a single eyelet, three-strut frame, scaffold with a filter coupled to the distal frame-cell edged of the present invention. FIG. 7B is a rotational isometric view of a single eyelet, three-strut frame, scaffold with a filter coupled to the distal frame-cell edged of the present invention. FIG. 7C is a perspective-isometric view of a single eyelet, three-strut frame, scaffold with a filter coupled to the proximal frame-cell edged of the present invention. FIG. 7D is a rotational isometric view of a single eyelet, three-strut frame, scaffold with a filter coupled to the proximal frame-cell edged of the present invention.

FIG. 8A is a perspective-isometric view of a dual eyelet, four-strut frame, scaffold with a filter coupled to the distal frame-cell edge of the present invention. FIG. 8B is a perspective-isometric view of a dual eyelet, four-strut frame, scaffold with a filter coupled to the proximal frame-cell edge of the present invention. FIG. 8C is a perspective-isometric view of a dual eyelet, four-strut frame, scaffold with a filter coupled to the proximal frame-cell edge in an off-set configuration and with the distal end of the porous section of the filter not being directly coupled to the distal eyelet, instead terminating proximal the distal eyelet according to the present invention.

FIG. 10A is a perspective-isometric view of a dual eyelet, three-strut frame, scaffold with an off-set filter coupled to the frame-cell of the present invention. FIG. 10B is a rotational isometric view of a dual eyelet, three-strut frame, scaffold with an off-set filter coupled to the frame-cell of the present invention. FIG. 10C is a perspective-isometric view of an uncoupled off-set filter of the present invention. FIG. 10D is a rotational isometric view of an uncoupled off-set filter of the present invention.

DETAILED DESCRIPTION

Figure 1B:
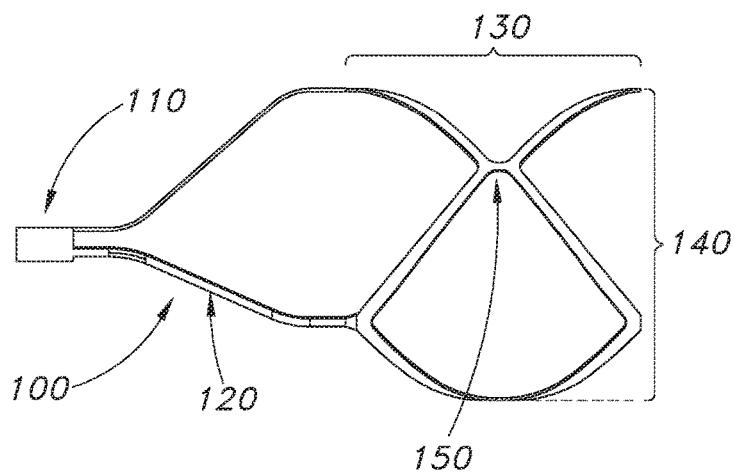
FIGS. 1A-1D show isometric views of an illustrative representation concerning the present invention.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "an insulator" can include a plurality of insulators.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the terms "biocompatible," "biocompatible material," "biocompatible polymer," or "polymer materials" refer to a synthetic or natural material that is, for example, non-toxic to biological systems and/or congruent with biological processes. In this respect, biocompatibility of materials with respect to the present disclosure denote minimal, negligible, or no risk of immunorejection, injury, damage and/or toxicity to living cells, tissues, organs, and/or biological systems. In illustrative embodiments, the biocompatible materials are one or more polymers or materials selected from, but not limited to, polyurethane, ETFE, polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, polylactic acid, polyglycolic acid, poly(lactide-co-glycolide), and/or poly(L-lactide), and the like, and combinations thereof.

As used herein, the term "composition" refers to a product, material, device or component with specified or particular materials, polymers, compounds, etc., in the specified amounts, as well as any products or the generation of such products which result, directly or indirectly, from combination of the specified items in the specified amounts.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another. In some embodiments, for example, coupling may include direct or indirect bonding, welding, linking, connecting, adhering, attaching and the like.

As used herein, the terms "cooperatively interact" or "cooperatively interacting" refer to the association of two or more adjoining components, where each component functions to facilitate the association. For example, a fitted plug would cooperatively interact with the component that the plug was fabricated to fit.

As used herein, the term "disease" or "medical condition" are used interchangeably and include, but is not limited to, any condition or disease manifested as one or more physical and/or psychological symptoms for which treatment and/or prevention is desirable, and includes previously and newly identified diseases and other disorders. For example, a medical condition may be any embolic associated disorder, such as, e.g., stroke, chronic cerebral ischemia, and/or pulmonary or myocardial infarction.

As used herein, the terms "disengage" or "disengaged configuration", both refer to act or state of no longer being securely associated or connected. For example, two components are disengaged with each other they are not in physical contact with each other. However, such components can be in contact while concomitantly occupying a disengaged state. In this circumstance, the components would not be securely engaged by such means as, for example, a locking mechanism. If such components are "reversibly disengaged" then the components are capable of engaging at a different time. The foregoing holds true for an engagement or disengagement with respect to an intravascular procedure employing devices and components of the present disclosure.

As used herein, the terms "disengage" or "disengaged configuration", both refer to act or state of no longer being securely associated or connected. For example, when two components are disengaged from each other, they are not in physical contact with each other. However, such components can be in contact while concomitantly occupying a disengaged state. In this circumstance, the components would not be securely engaged by such means as, for example, a locking mechanism. If such components are "reversibly disengaged" then the components are capable of engaging at a different time. The foregoing holds true for an engagement or disengagement with respect to an intravascular procedure employing devices and components of the present disclosure.

Moreover, embodiments of the present invention entail imperforated, filter ingress, regions configured with alternating apical and abapical embrasure sections or regions, which may be configured as, but not limited to, shapes selected from angled, straight, slanted, tapered, curved, diagonal, random, polygonal, rectangular, square, circular, curved, concentric, concave, perimetric, diamond, hexagonal, or triangular configurations, or any combination thereof.

As used herein, the terms "engage", "reversible engage", "reversibly engaged", and "engaged configuration" all refer to the act or state of being associated or connected in a secure manner for the purpose of joining two or more components for a period of time. For example, two components are engaged with each other when they are in contact and securely connected or associated for a period of time. To be in the engaged state, the components are in contact while concomitantly occupying an engaged state, such as, for example, a locked state. If such components are "reversibly engaged" then the components can be engaged and disengaged with respect to the features enabling such association and disassociation, respectively. The foregoing holds true for an engagement or disengagement with respect to an intravascular procedure employing devices and components of the present disclosure.

As used herein, the term "encapsulation" or "encapsulating" refers to the retention of substance within a compartment, delineated by a physical barrier. For example, the encapsulated components described herein refer to components which are retained within, and surrounded by a physical barrier.

It should be noted that the term "exemplary" as used herein to describe various embodiments is intended to indicate that such embodiments are possible examples, representations, and/or illustrations of possible embodiments, i.e., where such terms are not intended to connote that such embodiments are necessarily extraordinary or superlative examples with respect to the referred to embodiments of the present invention.

As used herein, the term "ischemia reperfusion injury" refers to the damage caused first by restriction of the blood supply to a tissue followed by a sudden resupply of blood and the attendant generation of free radicals. Ischemia is a decrease in the blood supply to the tissue and is followed by reperfusion, a sudden perfusion of oxygen into the deprived tissue.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an embolism. "Tissues" are singular or multiply-layered structures, i.e., monolayers or stratified layers of cells, which are organ constituents. One or more different tissues may form an organ or organs. An organ may also be composed of only one type of tissue or cell, or different tissues or cells.

As used herein, the term "polymer" refers to a macromolecule made of repeating monomer or multimer units. Polymers of the present disclosure are polymeric forms of, and include, but are not limited to, polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, polylactic acid, polyglycolic acid, poly(lactide-co-glycolide), poly(L-lactide), poly(hyaluronic acid), poly(sodium alginate), poly(ethylene glycol), poly(lactic acid) polymers, poly(glycolic acid) polymers, poly(lactide-co-glycolides), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(acrylic acid), poly(vinyl acetate), polyacrylamide, poly(ethylene-co-vinyl acetate), poly(methacrylic acid), polylactic acid, poly(L-lactide) (PLLA), polyglycolic acids, nylons, polyamides, polyanhydrides, poly(ethylene-co-vinyl alcohol, polycaprolactone, polyvinylhydroxide, poly(ethylene oxide), and polyorthoesters or a co-polymer or terpolymer formed from at least two or three members of the groups, respectively.

As used herein, "prevention" or "preventing" of an infection or condition refers to a method or indicator that, in a statistical sample, reduces the occurrence of the infection or condition in a sample patient population relative to an control sample patient population. As used herein, preventing an infection or condition includes the prevention of embolic disorders, e.g., stroke, cardiac arrest, etc.

As used herein, the general terms "proximal" and "distal" can be defined with respect to the location closest to and most distant from a catheter hub. Likewise, the term "proximal" may refer to the scaffold or frame end through which debris enters, via a filter ingress, to be collected by the associated filter.

As used herein, the term "reticulated material" refers to compositions or composition matrices composed of network constituents forming one or more layers or matrix configurations. For example, reticulated material include, but are not limited to, fiberglass, silicone, filter materials (as further detailed herein) one or more polymers, plastic, and resin materials, or any combination thereof.

As used herein, the terms "scaffold," "support," or "frame," used in the context of a structure that functions as an elastomeric frame with respect to the embolic protection devices disclosed herein, refer to structures configured intraluminally operate from collapsed and expanded profiles, while also possessing radial rigidity as needed. Such scaffolds have various contemplated compositions, which include, but are not limited to, nitinol, stainless steel, glass, metals, plastic, silicones, and/or other materials capable of functioning as an embolic protection device as disclosed herein.

As used herein, the terms "scaffold," "support," or "frame," used in the context of a structure that functions as an elastomeric frame with respect to the embolic protection devices disclosed herein, refer to structures configured to intraluminally operate from collapsed and expanded profiles, while also possessing radial rigidity as needed. Such scaffolds have various contemplated compositions, which include, but are not limited to, nitinol, stainless steel, glass, metals, plastic, silicones, and/or other materials capable of functioning as an embolic protection device as disclosed herein.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder characterized by an embolism if, after undergoing a procedure pursuant to the devices and methods of the present invention, the subject shows observable and/or measurable reduction in or absence of one or more signs and symptoms of a particular disease or condition associated with embolic disorders.

Overview

Cardiovascular indications, including acute vascular diseases, such as acute coronary syndrome, myocardial infarction, stroke, pulmonary embolism, deep vein thrombosis, peripheral arterial occlusion and other blood system thromboses constitute major health risks. Such diseases are caused by either partial or total occlusion of a blood vessel by a blood clot or other obstruction, which typically consists of fibrin and aggregated platelets, among other intravascular detritus. See Goldsmith, et al., "Regional cerebral blood flow after omental transposition to the ischemic brain in man: A five-year follow-up study." *Acta Neurochir* 106: 145-152 (1990).

Stroke is a leading cause of long-term disability in the U.S., while also accounting for one out of every twenty American deaths annually. See "Heart and Stroke Statistics," The American Heart Association, 2017. Stroke occurs when a blood vessel that brings oxygen and nutrients to the brain is either (i) clogged by a blood clot, or some other mass in the case of an ischemic stroke, or (ii) bursts pursuant to a hemorrhagic stroke. When an ischemic stroke occurs, the blood supply to the brain is interrupted, and thus brain cells are deprived of glucose and oxygen required for proliferation. As a result, brain cells in the affected region are damaged, where the extent of such damage typically depends on how long brain cells are deprived of essential blood nutrients, including oxygen. In the absence of oxygen for only a few minutes, brain cell function becomes inevitably lost, which in many cases leads to patient death.

Ischemic stroke is the most common type of stroke accounting for about 87% of all strokes. See id. When a thrombus forms and blocks arterial blood flow to the brain, such strokes are clinically defined as thrombotic ischemic strokes. Embolic ischemic strokes, however, refer to the blockage of an artery by an embolus, a traveling particle or debris mass in the arterial blood stream emanating from the distal vasculature. Emboli most commonly arise from the vascular penumbra of the heart, especially in conjunction with associated atrial fibrillation, but particularly in a perioperative manner pursuant to an intervention procedure. Embolizing particles may nevertheless originate from most any branch of the vascular arterial tree.

Specific treatment of embolic associated disorders, including stroke and various other cardiopulmonary or vascular diseases, may include thrombolytic agents, antiplatelet drugs, anticoagulants, and surgery. Such interventions, however, harbor their own risks, where many surgical treatments merely recapitulate the embolic cycle by liberating secondary embolic debris that eventually occlude the downstream vasculature, thereby resulting in continuous procedural complications and poor patient outcomes. The import of embolic prophylaxis is accordingly manifest.

Embolic protection devices of the present disclosure are therefore employed to capture and remove dislodged debris. These devices are typified by a matrix or scaffold structure that maintains an operative measure of blood vessel patency while apposing the vessel lumen. Coterminous with the embolic device scaffold is a capture or filter component or "basket" that conforms to the vessel wall and maintains full-wall apposition during an intervention in illustrative embodiments. Blood flow in this regard is directed into the filter, which typically possesses a conical design, thereby effectively capturing debris while maintaining perfuse blood flow.

Radiopaque indicators, such as, e.g., gold or tungsten markers, are coincident with the filter in many embodiments to allow for precise fluoroscopic positioning and verification of apposition prior to proceeding with an intervention. Insertable guides, guidewires, and/or capture wires function to enhance control and stability of the filter during the procedure as well. And, while myriad indications are envisaged for employing such devices, some of the most common indications include lower extremity procedures, where, together with a guidewire, the embolic devices of the present disclosure are used for standalone procedures or in concert with percutaneous transluminal angioplasty (PTA) or stenting, i.e., in therapeutic regimens directed towards the treatment of severely calcified lesions in arteries of the lower extremities. In these applications, the vessel diameter at the filter basket placement site is from about 2-7 mm in some embodiments.

Likewise, the present devices and methods are indicated with respect to saphenous vein graft (SVG) procedures, where removal of thrombi and related debris is required. The devices also act in conjunction with guidewires in certain embodiments, when percutaneous transluminal coronary angioplasty or stenting procedures are performed in coronary saphenous vein bypass grafts with reference vessel diameters in accord with the foregoing lower extremity procedures. Embolic prophylaxis is also indicated for carotid procedures involving angioplasty and stenting of the carotid arteries. The diameter of the artery at the site of the filter basket placement is about from 3-7 mm in some embodiments.

In sum, thrombus, atheroma, lipids, and plaque embolizing to the brain, lungs, or the vasculature penumbra of other vital organs can be a fatal consequence of cardiopulmonary procedures. Such circulating embolic material arises, in many instances, pursuant to various surgical procedures requiring trans-catheter manipulations, among other clinical interventions. These unintended consequences of intraluminal medical procedures are nevertheless a fundamental risk attendant to such surgeries that, in most cases, can be mitigated. Embolic prophylaxis by capture or collection of antegrade-flowing embolic debris, as detailed pursuant to the present disclosure, substantially improves the overall outcome and survival of patients that require any of the foregoing cardiopulmonary procedures.

Embolic Devices, Components and Embodiments

Conventional embolic protection devices typically function as an intervening barrier between the source of the clot or plaque and the downstream vasculature. Issues such as lack of deployed low profile, structural rigidity, and filter integrity, e.g., the ability of the filter to sustain maximal influent capacity, while maintaining its porosity and structural conformation, nevertheless plague such traditional devices, some of which are described in the following patent publications, which are hereby incorporated by reference in their entirety: U.S. Patent Publication Nos. 2004/0215167 and 2003/0100940; and U.S. Pat. Nos. 6,371,935; 6,361,545; 6,254,563; 6,139,517; 6,537,297; 6,499,487; 5,769,816; and PCT International Publication Serial No. WO 2004/019817.

With respect to the foregoing and other conventional embolic protection practices in general, each system has its own intrinsic limitations, and protection afforded by those devices is less than complete in many instances. For example, inefficacious embolic protection, in many instances, is borne out of oversized device profiles that in fact lead to embolization, i.e., rather than obviating embolism formation. Likewise, incomplete filter apposition or conduit occlusion—and particularly in bending vessel segments—lack of secondary branch protection, incomplete aspiration, inadequate filter pore size, device mediated vessel wall trauma, side branch backwash during occlusion versus siphoning of debris during filtering, and delayed platelet-white cell embolization from the target site, are all facets of inefficacious embolic protection. See, e.g., Sangiorgi and Colombo, "Embolic Protection Devices," *Heart*, Vol. 89(9), pp. 990-92 (2003).

In this respect, numerous devices and methods of embolic protection have been used adjunctively with percutaneous interventional procedures to date. These techniques, although varied, each falter with respect to one or more of the following features, i.e., features that are desirable for embolic protection, which include intraluminal delivery, flexibility, trackability, small delivery profile to allow crossing of stenotic lesions, dimensional compatibility with conventional interventional implements, ability to minimize flow perturbations, thromboresistance, conformability of the barrier to the entire luminal cross section, and a means of safely removing the embolic protection device and trapped particulates. The devices and methods of the present disclosure, however, achieve the foregoing attributes as detailed herein and below.

Currently, there are two general strategies for achieving embolic protection, (i) techniques that employ occlusion balloons, and (ii) techniques that employ an embolic filter. Balloon occlusion devices, however, may cause distal ischemia that may not be well tolerated by some patients, while associated aspiration catheters may not retrieve all the particles trapped in the artery. On the other hand, the use of embolic filters is desirable to the extent that achieving embolic protection does not inhibit continuous perfusion of blood. And, while many conventional filter devices possess a finite lower end particle-capture size threshold, the present invention embodiments are not so limited.

In this respect, the present technology relates to, inter alia, novel embolic protection devices and methods that entail a scaffold structure composed of struts and at least one eyelet, having an eyelet axis of radial symmetry extending therethrough, i.e., an eyelet axis. Extending from a distal eyelet, the struts form an elastomeric lattice or frame adapted to operate between an expanded and a collapsed profile in suitable embodiments. Coupled to the elastomeric frame of the scaffold, in suitable embodiments, is a conical or tapered filter having an imperforated section for attachment to the frame and a porous section possessing a plurality of perforations, which thereby enables the fluid passage of blood through the filter. The filter in some embodiments has a conical shape tapering toward the distal end of the embolic protection device, which opposes a proximally located fluid ingress.

The conical conformation of the present filters imparts a structure possessing a robust internal embolic capture volume that is markedly enhanced compared to many conventional devices—depending on particular applications and procedure indication—which accordingly provides for the collection of substantially all emboli and related detritus liberated during a surgical procedure. For example, depending on a particular indications, e.g., SVG, ceratoid, lower extremity, etc., the filter size or lumen apposition diameter ranges from about 0.1, 1, 3, 5, 7, 9, and 10 mm to about 0.5, 1, 3, 5, 7, 9, 10, 15, and 20 mm, in some embodiments. In illustrative embodiments, the filter size or lumen apposition diameter ranges from about 3-7 mm.

In accord, such extended filter volumes allow for a greater perforation or pore surface area compared to traditional devices. As such, in concert with an increased number of filter pores or perforations, the breadth of the filter area enables the application of various pore size diameters, i.e., depending upon the requirements associated with an intended medical procedure. Taken together, the foregoing attributes permit a functionally adaptable filter-scaffold structure that confers a surgeon with the ability to specifically select a "personalized" or procedure-specific device for functional efficacy.

Control over the frequency and dimension of a filter's porosity imparts a system of selectable parameters that function in accord with other attendant aspects of surgical interventions requiring embolic protection, such as, e.g., maintaining scaffold adhesion during deployment and retrieval, while also decreasing antegrade flow pressure. To this end, minimizing back-flow pressure is a vital aspect of embolic protection applications that are adapted for use in high-flow vascular or aortic locations—areas in which larger blood volumes and/or pressures are commonly found—at least insofar as the increased cardiac output required pursuant to such back pressure gradient formation can further confound surgical intervention for patients with heart disease or other pre-surgical infirmities.

The filters of the present invention relate to compositions and configurations concerning one or more of, but not being limited to, conical filter configurations, asymmetric conical or oblique filters, filter ingress configurations, imperforated filters and sectional regions thereof, filters possessing embrasures, perimeter embrasures and/or ingress embrasures, offset filter embodiments, filters internal or external to an elastomeric frame, laser perforated filters, filter meshes, capture membranes, polymeric materials, braided wires, and/or tapered filters, etc. In this respect, such filters are composed of a material, in illustrative embodiments, selected from, but not limited to, polymers, fluoropolymers, polytetrafluoroethylene (PTFE), ePTFE, polyurethane, polyethylene, polypropylene (PP), polyvinylchloride (PVC), polyamide (nylon), polyethylene tetraphlalate, polyetherether ketone (PEEK), polyether block amide (PEBA), polytetrafluoroethylene (PTFE) and combinations thereof. Additional or alternative filter materials are disclosed in, for example, but not limited to, U.S. patent application Ser. Nos. 08/553,137; 08/580,223; 08/584,759; 08/640,015; 08/645,762; and U.S. patent application Ser. No. 08/842,727, all of which are hereby incorporated by reference in their entirety.

The membrane filters of the present disclosure are alternatively composed of a mesh screen entailing several woven or braided wires. These woven or braided wires may be made of any number of suitable biocompatible materials such as stainless steel, nickel-titanium alloy or platinum. Likewise, some embodiments may include filters composed of a metals, polymers and/or other constituents that are knitted, woven, or nonwoven fiber filaments and/or wires, in some embodiments. It will be appreciated that various regions, portions, layers, overlapping configurations, etc., of the filters of the present invention may be constructed of an impermeable or imperforated material or section for increased directional fluidity with respect to the blood influent, as further detailed herein and below.

Along the same lines, the filter material may be composed of two or more different materials, each of which can have distinct filter capacity and/or coupling characteristics. The filters of the present disclosure may possess a uniform or asymmetrical pore distribution and/or pore-size diameter. Briefly, illustrative embodiments entail filters having perforations possessing a pore size diameter ranging from about 5 μm to about 200 μm. The pore diameter of the perforations, in illustrative embodiments, may also range from about 0.001, 0.01, 0.1, 1, 0.25, 0.5, 0.75, 1, 3, 5, 7, 9, 10, 15, 20, 30, 50, 100, 300, or 500 μm to about 0.5, 0.75, 1, 3, 5, 7, 9, 10, 15, 20, 30, 50, 100, 500, or 900 μm. In other embodiments, the pore diameter is from about 0.001, 0.01, 0.1, 1, 0.25, 0.5, 0.75, 1, 3, 5, 7, 9, or 10 μm to from about 0.5, 0.75, 1, 3, 5, 7, 9, 10, 15, 20, 30, 50, or 100 μm.

The filter perforations, as noted above, are constituted in some embodiments via laser-cutting techniques or are similarly manufactured through the use of stamping, photoetching, or other cutting techniques that provide for and maintain the integrity of the filter, while facilitating the collection of embolic debris. In some embodiments, the manufactured filter perforations range in number from about 5 to about 5,000. In suitable embodiments, the number of perforations embedded in the filters of the present invention range from about 1, 250, 500, 1,000, 3,000, 5,000, or 10,000 to about 500, 1,000, 5,000, 10,000, or 50,000. In suitable embodiments, the laser cut embedded filter possess about 100-250 perforations. Certain filter embodiments possess a perforated filter area of about 3-8 in$^2$, while also having a proximally located imperforated section of about 2-5 in$^2$, where the imperforated section is attached to the scaffold frame as detailed herein.

In the same regard, the filter compositions and materials are formed to a desired filter shape, e.g., conical, asymmetric or oblique, proximally tapered, etc., by first laser-cutting the material to a desired specification, and thereafter circumferentially conforming the material to an interior and/or exterior region of the scaffold frame. The filter is coupled, attached, connected, adhered, bonded, welded, sonic welded, UV treated, and/or extruded, and the like, etc., to the scaffold-frame struts in some embodiments. In a similar fashion, the proximal and/or distal eyelets may be coupled to the various frame or strut components per the heretofore delineated techniques, and those known in the art.

The filters of the present disclosure, moreover, can be coupled to the scaffold-frame, as further discussed below, via a variety of methods as noted above, which also include, for example, mechanical bonding, solvent or adhesive bonding and/or over-molding in an arrangement such that the scaffold frame struts are placed in a topological mold, where the polymer material is subsequently incorporated therein to form a bond at the interface between the scaffold frame strut and the polymeric filter material. Additionally or alternatively, the filter can be attached, coupled, affixed, etc., onto or bonded to a scaffold-frame, by any number of suitable attachment means in addition to the foregoing, such as, but not limited to, extrusion, crimping, soldering, bonding, welding, brazing or any combination thereof. With respect to the single eyelet embodiments detailed below and herein, insofar as the scaffold frames do not extend into or substantially envelope the filter in such embodiments, the frame-cell cross-sectional area provides support to reduce the filter crush profile. In addition, the filter material may also be bonded to either the outer or inner cell designs of the frame-cell as shown in FIGS. 7A-7D, and as discussed below and herein.

The elastomeric frames of the present invention are adapted to operate between expanded and collapsed profiles, as noted above, where the frame includes struts extending from the proximal eyelet to define a proximal strut region, and a frame-cell region having a first edge that is continuous with the proximal strut region. Various embodiments of the present invention also entail a scaffold having a second, distal eyelet, which is similarly oriented about the eyelet axis and thereby defines a distal scaffold end, which will be further detailed herein and below. Distal struts, moreover, accompany embodiment configurations possessing a distal eyelet, where such distal struts extend from the distal scaffold end to define a distal strut region that is continuous with an edge of the frame-cell region.

The frame-cell struts, in some embodiments, are composed of various materials, including, but not limited to, Nitinol, stainless steel, polymer-based compositions, radiopaque materials, e.g., tantalum, platinum, and/or palladium, metals, nickel alloys, shape memory alloy materials, e.g., NiTi alloys, and/or any other suitable biocompatible materials, and combinations thereof. Additionally or alternatively, synthetic polymers are attractive scaffold-matrix materials because they can be readily manufactured with a wide range of reproducible, biocompatible structures. These scaffold-frame structures can vary in composition, while still providing sufficient mechanical support for withstanding compressive, radial and/or tensile forces. In addition to the materials disclosed above and herein, self-expanding materials may also be used, in illustrative embodiments, such as those disclosed in U.S. Pat. Nos. 4,795,458; 5,037,427; 5,089,005; and 5,466,242, the disclosures of which are hereby incorporated by reference in their entirety.

Maintaining the shape and integrity of the elastomeric frames of the present invention is essential for embolic prophylactic applications of the present technology. The elastomeric frames in this respect provide exceptional vessel wall apposition when deployed in an expanded state, while ensuring that the collapsed configuration possess a low profile, which is essential for filter and device control during deployment and retrieval. In some embodiments, a biocompatible nitinol polymer composite is laser cut to specific parameters prior to filter coupling or attachment. As noted above, the filter is accordingly coupled to at least a portion of the frame-cell region to form the embolic protection device.

In some embodiments, the imperforated section or region of the filter is coupled to the interior of the scaffold frame, while in other embodiments, it is coupled to an exterior region of the scaffold frame. Various other coupling or attachment configurations are within the scope of the present disclosure, including, but not limited to, coupling the filter to all or less than all of the scaffold frame struts, either via an interior or exterior attachment mechanism. In certain embodiments, moreover, one or more filter layers are provided, while some embodiments provide for inverted or everted filters. The scaffold frame struts may also include a connecting member in some embodiments, such as, e.g., one or more hooks, loops, seals, rivets, snapping components, screw fixtures, clamps, adhesives, locks, friction fitting components, and the like, or any combination thereof, to connect or couple to the filter.

The connecting member, to this end, may also be thermally treated to form an engagable component that connects to or with the various components of the embolic protection devices disclosed herein, such as, e.g., the eyelets, struts, frame-cell regions, and the filter. Likewise, the connecting or attachment member may be directly bonded to the filter in the same manner as the filter is coupled to the frame-cell, i.e., if no attachment member were present. In some embodiments, the connecting or attachment member, when present, is a helical or looped structure that encompasses the end of a strut and forms an attachment locus that consequently couples to the imperforated filter region.

Such attachment member connections engage and secure the struts against the imperforated section of the filter, which accordingly provides for a pliable, high-surface area portion, for connection to the filter. In addition to the foregoing, the distal edge of the scaffold frame-cell region can be fixed to the imperforated filter section via a component or mechanism, such as, for example, a crimped sleeve or other distinct component that facilitates the attachment of the filter to the frame. In illustrative embodiments, the imperforated section is composed of alternating embrasure segments disposed about an eyelet axis of radial symmetry to define a coupling configuration, as further detailed herein.

After forming the substantially resilient, yet compressible, scaffold-frame-filter structure, it may be employed for a particular procedure, in conjunction with one or more of the following, in certain embodiments, i.e., depending on the intended procedure, an associated or integral radiopaque marker for fluoroscopic visualization, a hypotube connector, flushing needle, one or more guidewires, e.g., primary, capture and retrieval guidewires, associated catheters and/or sheaths, among other components as known in the art for particular procedures. While the present disclosure, in some embodiments, typically does not require the use of an inflatable balloon, i.e., due to the resiliency of the frame composition, related PTA or other angioplastic applications may require the use of such balloons. Nevertheless, in illustrative embodiments, a catheter balloon and/or sheath may be employed or omitted as necessary. The scaffold frame is compressed in some embodiments, directly onto the catheter, when used, and a sheath may be positioned over the frame to prevent it from expanding until deployed, in certain embodiments.

Along the same lines, some embodiments of the embolic protection devices of the present disclosure further include one or more insertable guides and/or guidewires extending through the proximal eyelet, the hollow volume formed by the elastomeric frame, and, when applicable, the distal eyelet. The insertable guide facilitates deployment and directional positioning of the device along the eyelet axis alone or in conjunction with a guide catheter. To this point, the embolic protection devices of the present disclosure are typically deployed intravascularly and retrieved upon procedure completion using deployment and retrieval catheters, which are similarly positioned intravascularly. Such deployment and retrieval catheters and other intravascular devices as will be needed will be familiar to one skilled in this art.

Turning now to the figures, the single eyelet embodiments of the present invention are shown by way of example in FIGS. 1-2 and 7. In this respect, a three strut scaffold 101, as shown in the three-dimensional representation of FIG. 1D, is provided. The isometric views pertaining to FIGS. 1A (isometric view) and 1B (rotational side-view), show a strut 120 extending from proximal eyelet 110, where struts 120 (a), 120(b) and 120(c) are orientated about an axis of radial symmetry, i.e., an eyelet axis, at an approximate 45° angle, which is referred to herein as a primary strut configuration. Nevertheless, embodiments of the present invention include strut angles-relative to the eyelet axis-ranging from 1° to 90°.

Figure 1C:
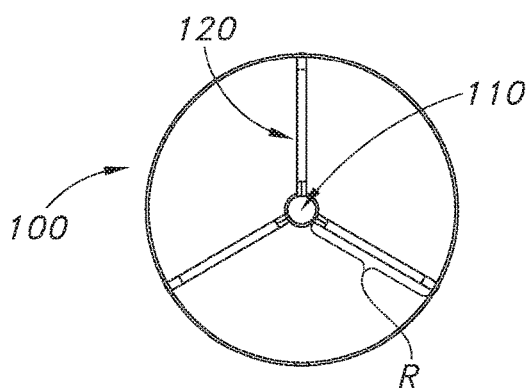
Figure 1A:
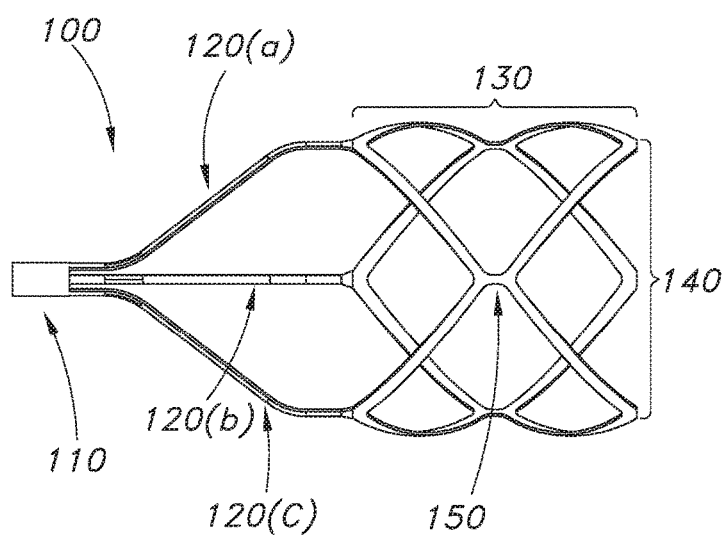
Figure 1D:
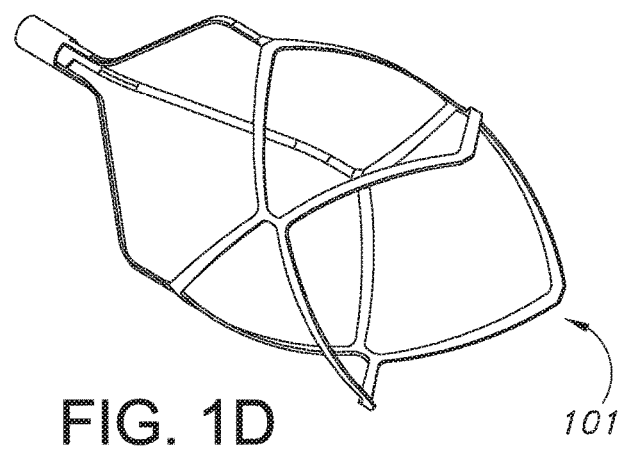

The individual struts extend from the proximal eyelet 110 to meet frame-cell region 130, which is defined by a lattice network of intersecting frame-cell struts 150 that terminate at the distal edge of embodiment 100, as shown in FIGS. 1A and 1B, at 140, which also defines an internal diameter of the scaffold. FIG. 1C shows an orthogonal end-view configuration of embodiment 100 with eyelet 110 and strut 120 noted in addition to radius R, which is coincident with the depth of an individual strut 120 from the radial circumference to the eyelet axis, i.e., half of diameter 140 as noted in FIGS. 1A and 1B.

Figure 2A:
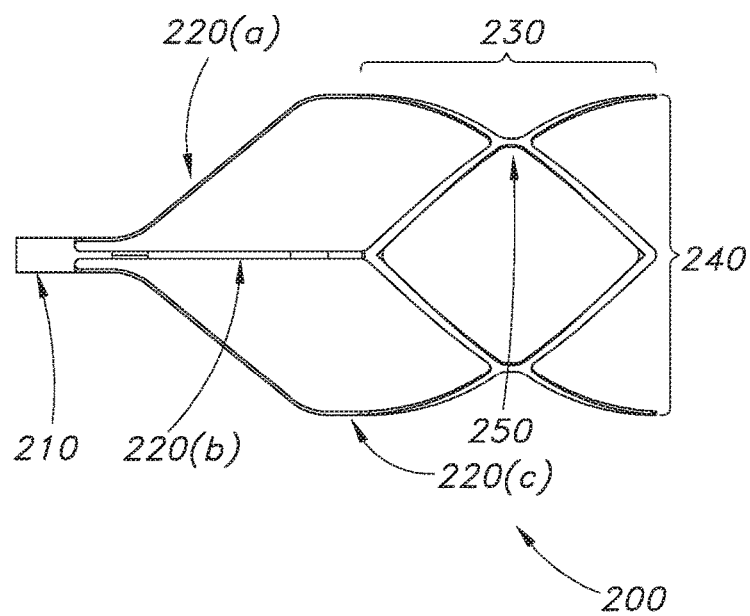
FIGS. 2A-2C show isometric views of an illustrative representation concerning the present invention.
Figure 2B:
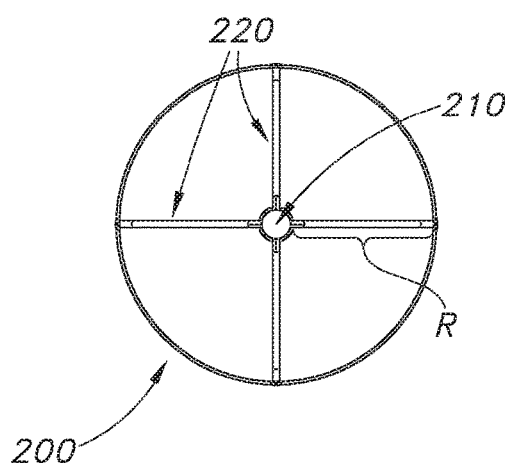
Figure 2C:
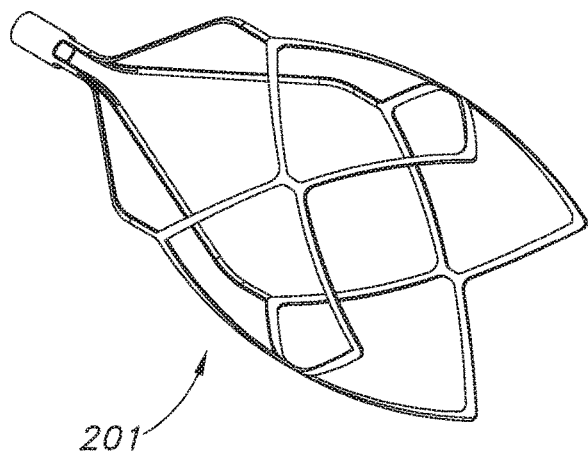
Figure 3A:
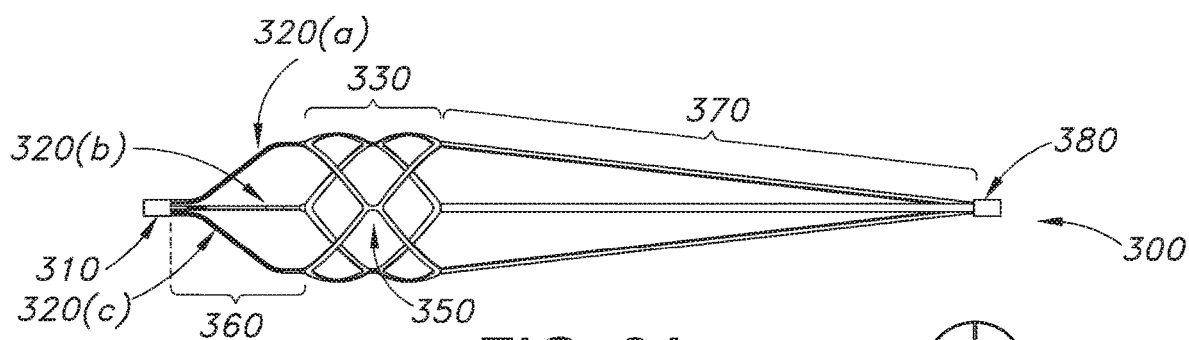
FIGS. 3A-3C show perspective-isometric views of an illustrative representation of the present invention.
Figure 3C:
Figure 3B:
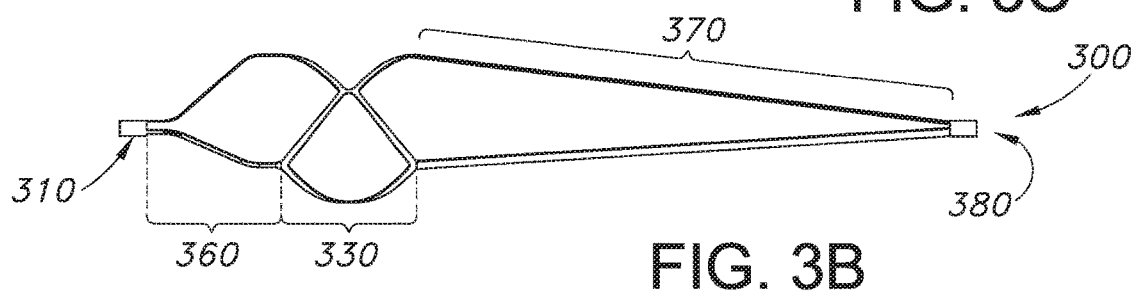

FIG. 2 shows a similar representative embodiment as illustrated in FIG. 1, except these embodiments 200, 201 depict four-strut scaffolds, as shown in the three-dimensional representation 201 of FIG. 2C. The isometric view pertaining to FIG. 2A shows struts extending from proximal eyelet 210, where struts 220(a), 220(b) and 220(c) are orientated about an axis of radial symmetry, i.e., an eyelet axis, at an approximate 45° angle to define a primary strut configuration. The individual struts extend from the proximal eyelet 210 meeting frame-cell region 230, which is defined by a lattice network of intersecting frame-cell struts 250 that terminate at the distal edge of embodiment 200, as shown in FIG. 2A at 240, which also defines the internal diameter of the scaffold. FIG. 2B shows an orthogonal end-view configuration of embodiment 200 with eyelet 210 and strut 220 noted in relation to radius R, which is coincident with the depth of an individual strut 220, i.e., half of diameter 240 as noted in FIG. 2A.

The embodiments above concern three and four-strut configurations of the scaffold structures of the present disclosure, yet the devices herein are not so limited. Any number of struts may be employed in this regard insofar as sufficient radial rigidity is maintained in concert with a low device profile. As such, some embodiments of the present invention contain any number of struts, including proximal and/or distal struts, as further detailed herein, frame-cell strut configurations, lattice regions, attachment components, embrasure attachment components, and the like, where such components range from about 1, 2, 3, 4, 5, 6, 7, 8, 9, 10, 15, 20, 30, 50, or 100, to about 2, 3, 4, 5, 6, 7, 8, 9, 10, 15, 20, 30, 50, 100, or 150 struts or other components noted above. In some embodiments, there are about from 2-8 struts or other components noted above with respect to the devices and scaffolds of the present invention.

Concerning the single eyelet embodiments detailed above and herein, insofar as the scaffold frames do not substantially extend into or circumferentially surround the filter in such embodiments, the frame-cell cross-sectional area provides for a reduced filter crush profile. In addition, the filter material may also be bonded to either the outer or inner cell designs of the frame-cell as discussed above and shown in FIGS. 7A-7D.

To this end, the tapered or conical filter is coupled to a distal frame-cell edge, in some embodiments, as shown in FIG. 7, which highlights perforations 725 that allow for high volume blood flow while capturing embolic debris. Because the elastomeric distal frame-cell edge is coterminous with the beginning of the filter, i.e., the filter ingress, in some embodiments including the single eyelet configurations, in conjunction with expandable resilience of the scaffold frame, it is the blood flow that in fact expands the entire filter volume upon deployment. The same holds true for the dual eyelet configurations detailed below at least insofar as such embodiments entail attachment and positioning of the filter internal to the scaffold frame.

In other words, certain embodiments of the present device and filter configurations do not solely rely on the elastomeric frame or other component of the scaffold matrix to maintain an expanded filter profile. Indeed, the blood flow influent coupled with the internally disposed resilience of the filter function to maintain filter ingress extension and distention, in illustrative embodiments. One advantage to such a device-filter configuration is that the integrity of the filter, e.g., porosity, contiguity, and secure capture profile, is sustained without significant disruptive constraints acting on the filter, i.e., via compressive, tensile, and/or radial frame-cell forces, other than blood flow.

Briefly turning back to FIGS. 1-2, the internal diameter of the scaffold embodiments are respectively enumerated 140 and 240. This diameter is substantially coincident with the diameter of the filter ingress—depending on the circumference of the ingress with respect to its attachment configuration—internal or external to the frame-cell region struts. In this regard, FIG. 7 shows representative embodiments of single eyelet 710 scaffold frames with three struts extending therefrom. The scaffolds of the present disclosure, however, can be cut to achieve various structures composed of anything from two to twenty-four or more strut configurations, as noted above, to alter the performance with respect to the filter and the overall profile of the embolic protection devices disclosed herein. In illustrative embodiments, the scaffold frames of the present disclosure possess from about 2 to about 6 struts.

Again referring to the filter-coupled single eyelet device configurations, as shown with respect to FIGS. 7A-7D, such tapered filters 700 entail imperforated filter embrasure sections 715 meeting and extending from a distal edge of frame-cell 730, where the functional porous section 705 terminates at filter end 711. Open frame-cell segments 715(a) of frame cell region 730 impart a distally oriented filter configuration as coupled to the frame. A distally oriented configuration in this regard, defines filter embodiments that are coupled or attached to a distal edge or region of a frame-cell scaffold section in a manner as detailed above. This relationship remains true whether a single or double eyelet configured scaffold is employed.

Figure 7A:
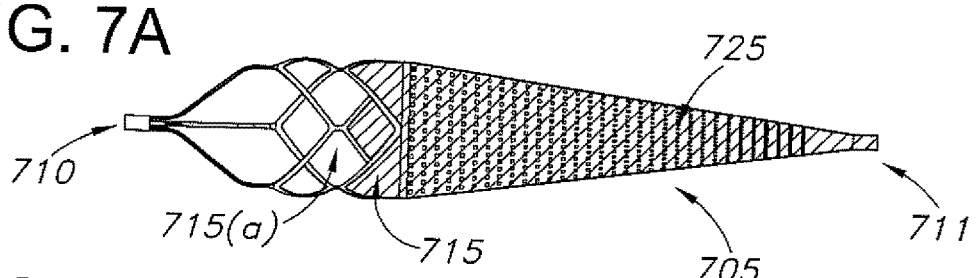
FIGS. 7A-7D show space-filled isometric views of an illustrative representation of the present invention.
Figure 7B:
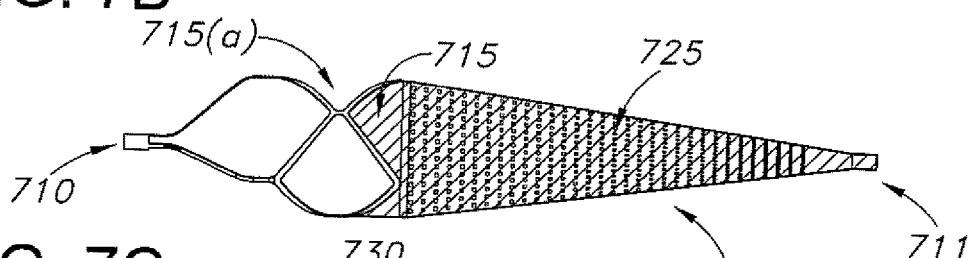
Figure 7C:
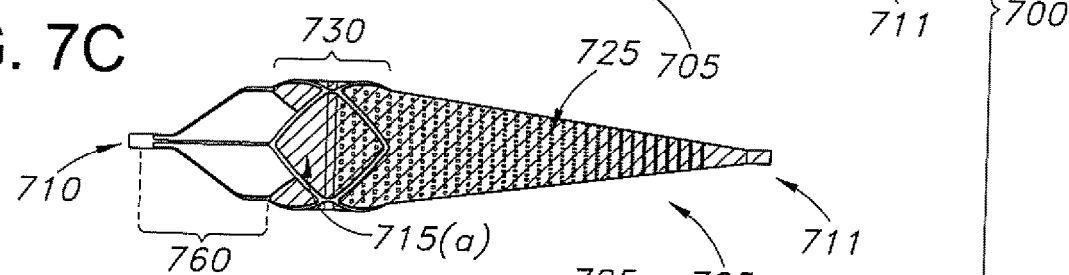
Figure 7D:
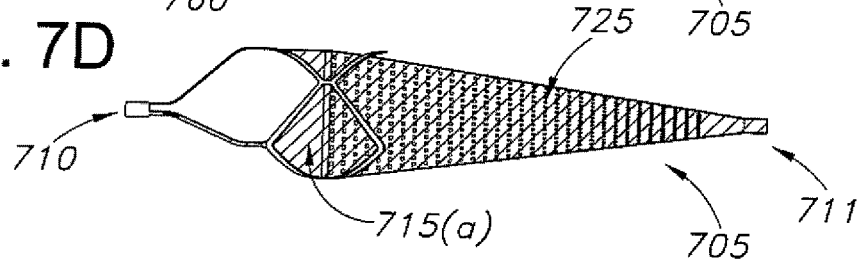

Specifically concerning FIGS. 7C-7D, tapered filters are shown with imperforated embrasure sections 715 attaching to and extending from a proximal edge or region of frame-cell 730, where the functional porous section 705 terminates at filter end 711. As described herein, a proximally oriented configuration in this respect, refers to filter embodiments that are coupled or attached to a proximal edge or region of a frame-cell scaffold section, which accordingly proximally shifts the entirety of the conical filter towards or within a greater region of the frame-cell. See, e.g., FIGS. 7C-7D. This relationship remains true whether a single or double eyelet configured scaffold is employed.

In some embodiments, the proximally shifted filter configuration provides a more ridged support lattice for maintaining confluence and filter integrity, including the extension of the filter ingress, with respect to the scaffold frame. Frame-cell region 715(a), with respect to FIGS. 7C-7D, are coterminous with or contain the embrasure segments 715 of the imperforated filter region, which imparts a proximally oriented filter configuration in comparison to the distally oriented configurations of the embodiments depicted in FIGS. 7A-7B.

Specifically concerning the embrasure segments, yet irrespective of any one set orientation of the filter with respect to the frame-cell, i.e., proximally or distally shifted or positioned, FIGS. 7A-7D denote triangular embrasures that circumferentially undulate to define the filter ingress in some embodiments. In addition to providing a seamless transition from the scaffold frame-cell region, the embrasures are configured as triangular sections of the imperforated filter region to enhance filter coupling and attachment to the respective frame-cell region, while also facilitating capture of embolic debris by directing or funneling the blood flow influent towards the tapering filter end. Specifically, filters that lack such configurations, i.e., such as a conical filter possessing a substantially uniform perimeter opening, in addition to having a decreased longitudinal support profile with respect to scaffold-frame attachment, would similarly possess a circumscribed ingress perimeter surface area, which consequently marginalizes the frictional constraints inherent to fluid dynamic systems such as those found in intraluminal vasculature systems.

Nevertheless, embodiments of the present invention entail imperforated, filter ingress, regions configured with alternating apical and abapical embrasure sections or regions, which may be configured as, but not limited to, shapes selected from angled, straight, slanted, tapered, curved, diagonal, random, polygonal, rectangular, square, circular, curved, concentric, concave, perimetric, diamond, hexagonal, or triangular configurations, or any combination thereof. In some embodiments, the imperforated, filter ingress, region possesses from about 1, 2, 3, 4, 5, 6, 7, 8, 9, 10, 15, 20, 30, 50, or 100 alternating apical or abapical embrasure segments, to about 2, 3, 4, 5, 6, 7, 8, 9, 10, 15, 20, 30, 50, 100, or 150 alternating apical or abapical embrasure segments. See FIGS. 7A-7D. In some embodiments, there are about from 2-8 alternating apical or abapical embrasure segments. In some embodiments, moreover, the imperforated-ingress region of the filter lacks one or more of the alternating apical or abapical embrasure segments, while in other embodiments, one or more of such embrasure segments are additionally configured to impart an offset filter embodiment as further detailed below and shown pursuant to FIG. 10.

As introduced above, illustrative embodiments of the present disclosure include scaffolds entailing a distal eyelet oriented about the eyelet axis, such that distal struts extend from the distal scaffold end to define a distal strut region that is continuous with a second or distal edge of the frame-cell region. In short, such dual eyelet configurations allow for enhanced control and operability of the filter material both during deployment and retrieval of the present devices pursuant to an interventional procedure. In particular, the filters in this respect are attached to an interior frame-cell region in accord with the single eyelet configurations detailed above, yet the second eyelet in this regard permits the elastomeric frame to readily lengthen when collapsed during insertion and retrieval, i.e., when a low profile configuration of the device is needed. Likewise, the additional structural rigidity associated with dual eyelet configurations are beneficial for procedures entailing the need for increased luminal apposition.

The dual eyelet embodiments of the present invention are shown by way of example in FIGS. 3-6 and 8-9. Briefly, a three-strut dual-eyelet scaffold 300, is depicted per the isometric views pertaining to FIGS. 3A and 3B (rotational side-view). Strut 320(a), 320(b) and 320(c) extend from proximal eyelet 310, where the struts are orientated about an axis of radial symmetry, i.e., an eyelet axis, at an approximate 45° angle in accord with the primary strut configurations noted above. The individual struts extend to meet frame-cell region 330, which is defined by a lattice network of intersecting frame-cell strut configurations 350 that are continuous with elongated distal struts, shown by the distal strut region 370, which extends to, and terminates at, the distal eyelet 380, as shown in FIGS. 3A and 3B. FIG. 3C shows an orthogonal end-view configuration of embodiment 300 with eyelets and struts depicted.

The proximal strut configurations illustrated in FIG. 3 concern a primary strut or eyelet configuration, where the struts are orientated about the eyelet axis at an approximate 45° angle. FIG. 4, however, depicts an inverted strut or eyelet configuration with respect to the same proximal features. Such a configuration facilitates vessel wall apposition and imparts a maximal frame-cell diameter or circumference immediate to the proximal eyelet to the extent that the inverted struts are orientated about the eyelet axis at an approximate 90° angle. The steeper slope of the inverted strut configuration provides for frame-cell induced vessel wall apposition to shift proximally—compared to the primary strut configuration—which allows for the capture of an increased volume of embolic particles.

Figure 4A:
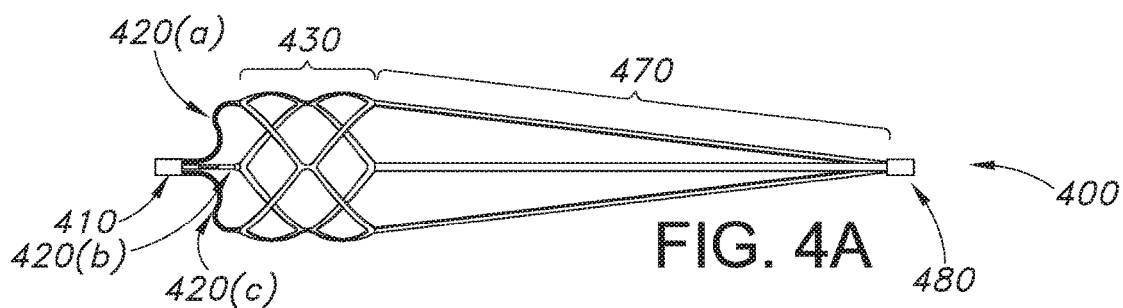
FIGS. 4A-4C show perspective-isometric views of an illustrative representation of the present invention.
Figure 4C:
Figure 4B:
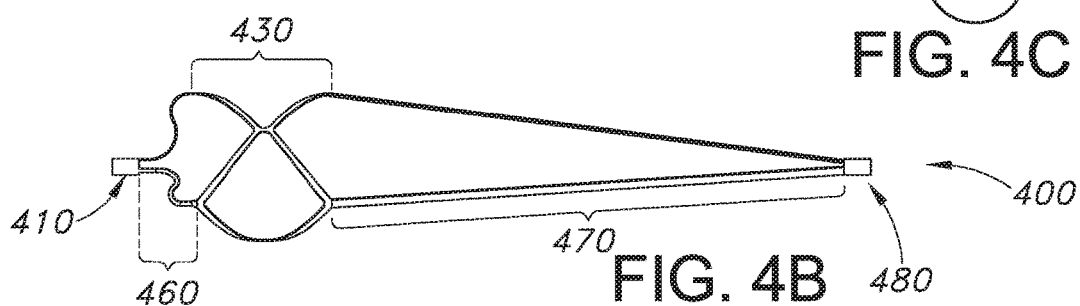

In accord with the foregoing dual-eyelet embodiments of the present invention, a three-strut inverted dual-eyelet scaffold 400, is depicted in FIG. 4. The isometric views pertaining to FIGS. 4A and 4B (rotational side-view), show struts extending from proximal eyelet 410, where individual struts 420(a), 420(b) and 420(c) are orientated about the eyelet axis, at an approximate 90° angle in accord with the inverted strut configuration of the present embodiments. The individual struts extend to meet frame-cell region 430, which is defined by a lattice network of intersecting frame-cell struts 450 that are continuous with elongated distal struts 470 extending to, and terminating at, the distal eyelet 480, as shown in FIGS. 4A and 4B. FIG. 4C shows an orthogonal end-view configuration of embodiment 400 with eyelets and struts depicted.

As depicted in FIG. 5A, a four-strut dual-eyelet scaffold 500 is shown, with FIG. 5B representing an orthogonal end-view configuration of embodiment 500 with eyelets and struts depicted. The isometric views pertaining to FIG. 5A, which are shown in the absence of an accompanying filter, similar to the embodiments above, proximal struts 520 extend from proximal eyelet 510, where the proximal struts are orientated about an axis of radial symmetry, i.e., an eyelet axis, at an approximate 45° angle. The individual struts extend to meet frame-cell region 530, where the distance from proximal eyelet 510 to the initial (proximal) edge of the frame-cell is defined by region 560, which is directly proportional to the foregoing strut angle inasmuch as the more gradual the strut radial slope, i.e., in accord with a lower strut angle, the longer the distance will be of section 560. Frame-cell region 530 is defined by a lattice network of intersecting frame-cell struts that are continuous with elongated distal struts 570 extending to, and terminating at, the distal eyelet 580, as shown in FIG. 5A. Individual elongated distal struts 590(a), 590(b) and 590(c) are enumerated, where the fourth strut cannot be seen insofar as it occupies the same longitudinal plane as 590(b), albeit at a distinct three-dimensional Cartesian depth.

As depicted in FIGS. 6A-6D, a proximal six-strut frame region with varying distal strut configurations 600 is shown, with FIG. 6D representing an orthogonal end-view configuration of embodiment 600 having eyelets and struts depicted. The filterless isometric views pertaining to FIGS. 6A-6C depict proximal struts, extending from proximal eyelet 610, orientated about an eyelet axis, at an approximate 90° angle to define an inverted strut configuration. The six proximal struts extend to meet frame-cell region 630, where the distance from proximal eyelet 610 to the initial (proximal) edge of the frame-cell is defined by region 660, which is directly proportional to the foregoing strut angle as noted above with respect to FIG. 5. In the inverted strut embodiments, because the proximal struts are configured to rapidly reach their maximal frame-cell diameter or circumference, i.e., immediate to the proximal eyelet, region 660 is relatively shorter compared to region 560 of FIG. 5, which shows a more gradual slope pursuant to the primary strut or eyelet configuration having an approximate 45° angle.

The six-strut frame-cell region 630, moreover, is defined by a lattice network of intersecting frame-cell struts that are continuous with six elongated distal struts, as defined in relation to distal strut region 670, which extends to, and terminates at, the distal eyelet 680, as shown in FIG. 6A. FIGS. 6B-C show the same inverted six-strut frame-cell region 630, as shown with respect to FIG. 6A, albeit with a distinct elongated distal strut region 690, where only two individual elongated distal struts are shown. In illustrative embodiments, the distal strut region is tapered towards the distal eyelet along the eyelet axis, and has a length of about 1.5 to about 10 times that of either or both of the proximal strut region and the frame-cell region.

The six proximal-two distal strut configuration, moreover, functions to maintain a low-profile, low mass scaffold region, while also providing sufficient rigidity for procedures requiring vessel apposition unsuitable for a single eyelet embodiment, yet do not necessitate the structural capacity of a continuous proximal to distal six-strut configuration, in illustrative embodiments. Insofar as the scaffold frames of the foregoing embodiments extend substantially around the filter, in addition to the frame-cell cross-sectional area, the elongated distal strut regions, however configured, impart a ridged support structure to reduce the filter crush profile. As before with the single eyelet embodiments, the filter material may also be coupled attached, or bonded to either the outer or inner frame-cell lattice designs as shown in FIGS. 8-10, and as discussed below.

Figure 8A:
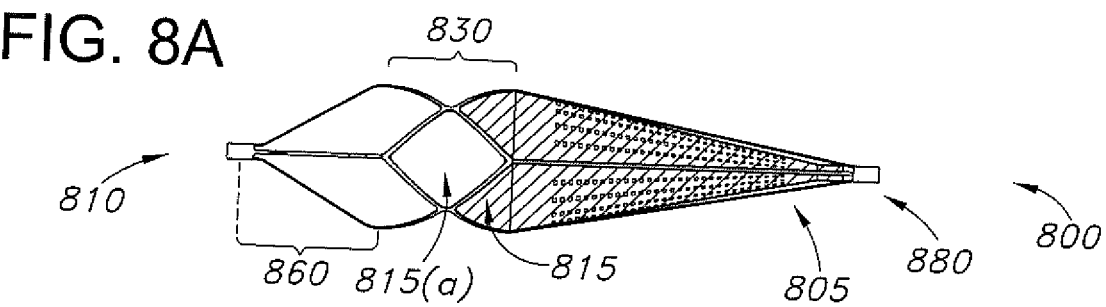
FIGS. 8A-8C show space-filled isometric views of an illustrative representation of the present invention.
Figure 9:
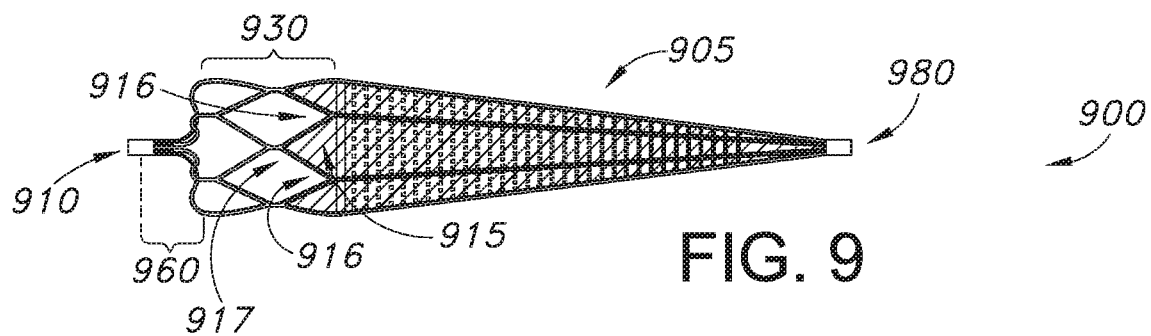
FIG. 9 is a space-filled isometric view showing the embrasures of a dual eyelet, inverted six-strut frame, scaffold with a filter coupled to the distal frame-cell edged of the present invention.

With respect to the dual eyelet embodiments detailed herein, the tapered or conical filter is coupled to the frame-cell edge, as shown in FIG. 8A, where the filter has perforations (not enumerated) allowing for high volume blood flow while capturing embolic debris. The blood flow, in this respect, enters the filter ingress and expands the filter upon deployment, i.e., inasmuch as the filter is disposed internal to the scaffold. Although externally disposed filter configurations—with respect to the dual eyelet scaffold frame structures—are within the scope of the present disclosure, and accordingly support or facilitate an expanded filter profile to an extent, the primary function of the dual-eyelet elastomeric frame configurations concerns the maintenance of structural rigidity and vessel wall apposition, i.e., any supporting function it inures to the filter is ancillary, yet nonetheless not negligible. The diameter of the frame-cell region, as before, is substantially coincident with the diameter of the filter ingress—depending on the circumference of the ingress with respect to its attachment configuration—internal or external to the frame-cell region struts.

Figure 8B:
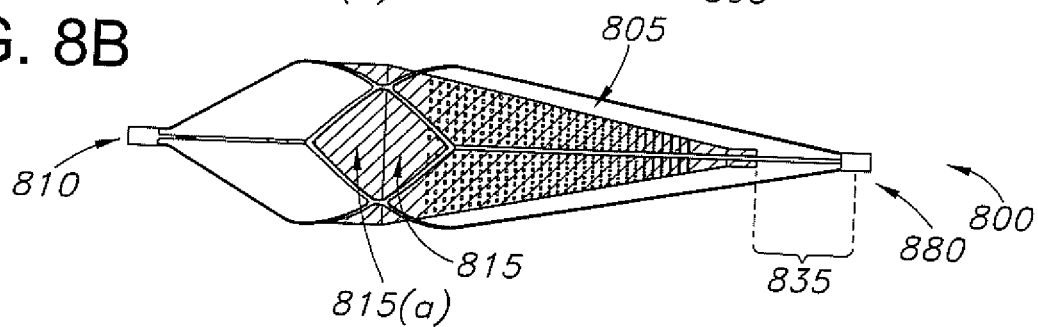

Referring now to the filter-coupled dual-eyelet device configurations, as shown with respect to FIGS. 8A-8B, such tapered filters 800 entail imperforated filter embrasure sections 815 extending from the attached frame-cell regions 830, where the remaining porous filter section 805 terminates at the distal eyelet 880. Open frame-cell segments 815(a) of frame-cell region 830 are shown with respect to the embodiment of FIG. 8A, which imparts a distally oriented coupled filter configuration. The distally oriented filter configurations as referred to herein relate to filters that are coupled or attached to the distal edge or region of a frame-cell scaffold section. As seen in FIG. 8A, the distal end of the filter abuts, or is adjacent to, the distal eyelet 880.

Figure 8C:
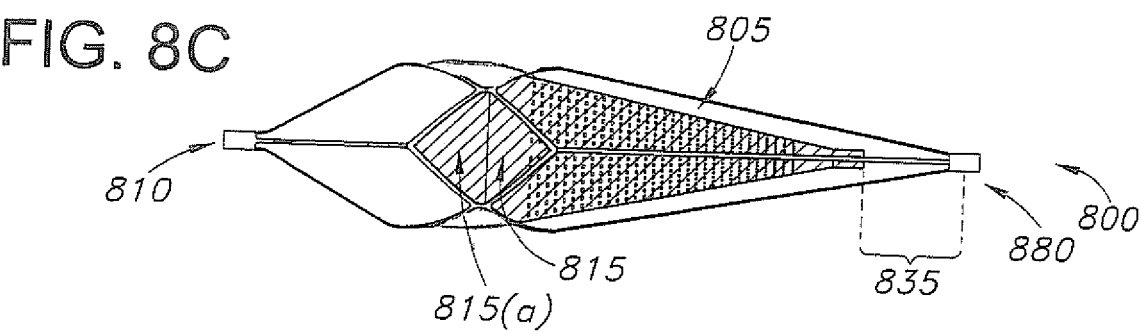

Concerning FIGS. 8B and 8C, conical filters are shown with imperforated filter embrasure sections 815 attaching to and extending from the proximal edge of frame-cell 830, where the remaining porous filter section 805 terminates at a distance 835 from the distal eyelet 880. Such a proximally oriented filter configuration refers to a filter of the present disclosure that is coupled to the proximal edge or region of a frame-cell scaffold section, which accordingly shifts the entirety of the conical filter towards or within a greater region of the frame-cell, while accordingly generating distance 835. Proximally shifted filter embodiments are advantageous insofar as such configurations allow for the filter to conform in the vasculature in relation to blood volume, i.e., as opposed to statically maintaining a direct conformal relationship with the frame alone as it expands and retracts in concert with the elastomeric frame. This allows the device and filter to better conform to the patient's vessel and attendant blood flow, which consequently reduces any unwanted stress that results in undesirable functionality of the device.

When in an expanded configuration, in suitable embodiments in this respect, the filter has a generally conical shape with the imperforated end portion, i.e., the ingress region. This ingress region has a substantially constant diametric profile that is structurally maintained through the frame-cell attachment, yet remains distally flexible with respect to a conformation adapting to the fluid dynamics pertaining to any particular volume or pressure of the influent blood source. Alternatively, in some embodiments, a reduced ingress profile is maintained. Here, after commencing deployment, the ingress end portion expands and generally follows the shape of the frame-cell region after the device filter has captured particles during a procedure. Subsequently, after the user begins retracting the filter, it cinches or closes around the proximal portion of any particles caught within the filter prior to any substantial reduction in diameter of the remaining, distal portions of the filter. In other words, the proximal end of the filter at least partially closes first, preventing the distal end of the filter from expelling captured embolic debris.

The foregoing relationships are facets of the filter configuration, i.e., whether it is proximally or distally shifted as shown in FIGS. 8A-8C, which may depend upon the particular needs for a particular procedure, e.g., whether a more ridged support lattice for maintaining the confluence of the filter and integrity of the filter ingress is required. Frame-cell region 815(a), with respect to FIG. 8B, contains or overlaps the embrasure segments 815 of the imperforated filter region, which imparts a proximally oriented filter configuration in comparison to the distally oriented configurations of the FIGS. 8A-8C embodiments. FIG. 8C shows the filter coupled to the proximal frame-cell edge in an off-set configuration with the distal end of the porous section of the filter not being directly coupled to the distal eyelet, instead terminating proximal the distal eyelet according to the present invention.

FIG. 9 shows a filter distally-coupled to an inverted six-strut dual-eyelet device embodiment 900. Briefly, the isometric view depicts six proximal struts, extending from proximal eyelet 910, orientated about an eyelet axis at an approximate 90° to define an inverted strut configuration. The six proximal struts extend to meet frame-cell region 930, where the distance from proximal eyelet 910 to the initial (proximal) edge of the frame-cell is defined by region 960, which is directly proportional to the foregoing strut angle. In these inverted strut embodiments, the proximal struts are configured to rapidly reach their maximal frame-cell diameter or circumference, i.e., immediate to the proximal eyelet.

Such tapered filters entail imperforated filter embrasure sections 915 extending from the attached frame-cell regions 930, where the remaining porous filter section 905 terminate at the distal eyelet 980. Open frame-cell segments 916 of frame-cell region 930 are shown with respect to the embodiment of FIG. 9, which imparts a distally oriented coupled filter configuration. The distally oriented filter configurations as referred to herein relate to filters that are coupled or attached to the distal edge or region of a frame-cell scaffold section. As seen in FIG. 9, the distal end of the filter abuts, or is adjacent to, the distal eyelet 980.

To the extent that the collapsing of embolic protection devices and their attendant filters has remained a pressing issue in the practice of percutaneous coronary and peripheral interventions, profile reduction is a key attribute of the present devices and filter delivery systems. See Sangiorgi and Colombo, "Embolic Protection Devices," Heart, Vol. 89(9), pp. 990-92 (2003). Certain filter materials in conjunction with their traditional deployment devices may fold and/or bunch, which accordingly increases the cross-sectional area as it enters the delivery system. See id. As such, the present devices and filters function to reduce any initial filter material entanglement in this regard by offsetting the filter with respect to where and how much of the filter is coupled to the frame-cell.

In this way, by positioning the filter material in non-uniform configurations at various locations about the frame-cell, it is possible to obviate such initial congestion of the filter material upon deployment into the delivery system. Such configurations, moreover, are designed to collect and hold embolic debris away from the vessel centerline. In this case, an asymmetric cone shaped filter is attached to the elastomeric frame, where the collected emboli will accordingly accumulate at the distal end of the conical filter and are held offset in the vessel, thus allowing relatively unperturbed flow at the vessel centerline.

As noted above with respect to the embrasure segments, and concerning the set orientation of the filter with respect to the frame-cell, i.e., proximally or distally positioned, the embrasures circumferentially undulate about the frame-cell to define the filter ingress in a uniform configuration, i.e., that is not offset. See FIGS. 7A-7D. In addition to providing a seamless transition from the scaffold frame-cell region, the embrasures are configured as triangular sections of the imperforated filter region to enhance the capture of embolic debris as noted above. In this regard, as shown in FIG. 10, the filter embrasure segments are incompletely connected or attached to both the proximal and distal frame-cell regions in an offset configuration.

Figure 10A:
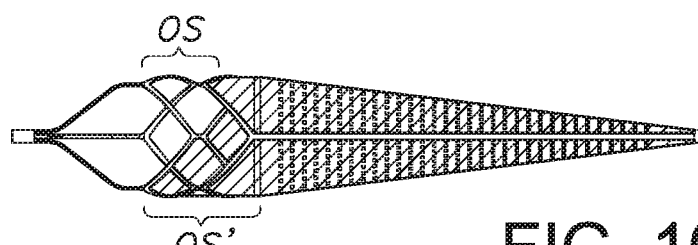
FIGS. 10A-10D show space-filled isometric views of an illustrative representation of the present invention.
Figure 10B:
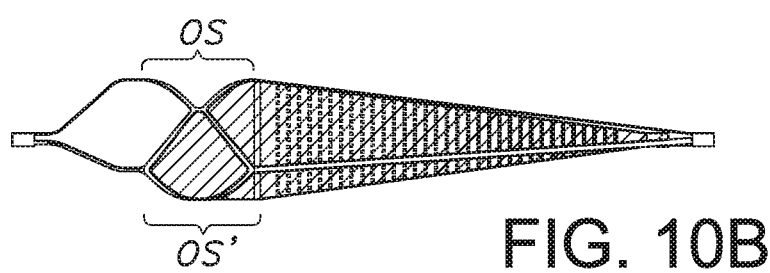
Figure 10C:
Figure 10D:
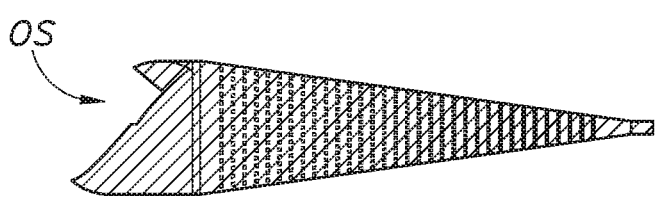

These offset filter configurations possess a general, three-dimensional, configuration of an asymmetric or oblique cone having a shape similar to that of a waffle cone, in some embodiments, which can be most clearly seen with respect to FIGS. 10C-10D. First referring to FIGS. 10A-10B, however, a three-strut, dual-eyelet, scaffold is depicted, where the conical filter is coupled to and disposed internally with respect to the elastomeric frame. Similar to above, the filter is composed of a perforated region distal to the frame-cell, while the imperforated section constitutes the offset portion of the filter that is coupled or attached to the scaffold.

The OS section of FIG. 10A and FIG. 10B (rotational side-view) is an open section of the proximal frame-cell region that is devoid of accompanying filter material. Nevertheless, the distal frame-cell region immediate thereto shows attached or coupled filter material. Concerning the same illustrations, the OS' section relates to the proximal frame-cell region diametrically opposed to OS, where the OS' imperforated filter embrasure segments are internally attached to both the offset proximal frame-cell region and the distal frame-cell region. FIGS. 10C-10D show the filter embodiment OS and OS' regions with the scaffold frame removed for clarity. Again, these offset filter configurations possess a general, three-dimensional, configuration of an asymmetric or oblique cone having a shape similar to that of a waffle cone, in some embodiments, which can be most clearly seen with respect to FIGS. 10C-10D.

In short, the embolic protection devices of the present disclosure entail a distally tapered filter that includes perforations for fluid flow therethrough, and an imperforated section that defines an ingress in some embodiments, while an integral scaffold includes a proximal eyelet defining a proximal end of the scaffold. A distal eyelet defining a distal end of the scaffold is provided in suitable embodiments, where both of the eyelets are oriented about a longitudinal eyelet axis, and an elastomeric frame disposed between the proximal and distal eyelets, where the frame has proximal and distal struts extending from their respective eyelets to respectively define proximal and distal strut regions, and a frame-cell region disposed between, and continuous with, the proximal and distal strut regions, where the imperforated section of the filter is coupled to at least a portion of the frame-cell region, where the filter is disposed internal to the scaffold, and an insertable guide extending through the elastomeric frame and each of the eyelets to facilitate deployment and directional positioning of the embolic protection device along the eyelet axis.

Methods and Applications

In one aspect, the present disclosure entails a method of preventing a disease or condition associated with the presence of an embolism in a subject in need thereof, the method entailing (a) selected a subject, (b) accessing one or more blood vessels of the subject, (c) deploying an insertable guide, where the insertable guide is unilaterally or bilaterally positioned, (d) deploying an embolic protection device over the insertable guide, where steps (c) and (d) are performed separately, sequentially or simultaneously, and where the embolic protection device includes (i) a conical filter having perforations for fluid flow therethrough, and an imperforated section that defines an ingress, (ii) an integral scaffold having a proximal eyelet defining a proximal end of the scaffold, and a distal eyelet defining a distal end of the scaffold, and where both of the eyelets are oriented about a longitudinal eyelet axis.

In accord, the methods further entail (iii) an elastomeric frame disposed between the proximal and distal eyelets, with respect to the embolic protection device employed according to the methods of the present invention, where the elastomeric frame has proximal and distal struts extending from their respective eyelets to respectively define proximal and distal strut regions, a frame-cell region disposed between, and continuous with, the proximal and distal strut regions, and where the imperforated section is coupled to at least a portion of the frame-cell region, (iv) where the insertable guide extends through the elastomeric frame and each of the eyelets along the eyelet axis, (f) capturing embolic debris, and (g) removing the embolic protection device with the captured debris from the subject's blood vessel to prevent the disease or condition associated with the embolism in the subject.

FIGS. 1-10, as discussed above, show various embodiments for the embolic protection device that each have an expanded configuration for trapping embolic particles and a contracted configuration which it adopts when being delivered through a delivery device, such as, but not limited to a catheter, micro-catheter or hypotube. The insertable guide in this regard extends through the one or more eyelet configurations and are connected to an expandable porous filter at one or more proximal regions, i.e., about the frame-cell region. In some embodiments, a 0.014-0.016 inch guidewire is provided with a polyurethane filter mounted at the distal end. The methods and systems of the present invention require, in some embodiments, both a delivery and a retrieval catheter. The filter, moreover, contains a pre-shaped nitinol expansion system that facilitates fluoroscopic visualization, accurate deployment, and vessel wall apposition.

The filter guidewire is placed within the delivery catheter and is passed through the target lesion, and the delivery catheter is subsequently withdrawn. Thereafter, the filter is deployed and crosses an intended lesion to reach a site approximately 3-10 cm distal thereto, the filter is expanded and routine angioplasty or other procedure is performed in some embodiments. As the blood passes through the filter, emboli are captured in the filter. At the end of the procedure, the filter is collapsed, trapping embolic debris, which are retrieved by retracting the wire into a retrieving catheter, in some embodiments. At this point, the entire device and its embolic contents are retracted. It will be readily apparent to those skilled in the art that various iterations of the foregoing methods, which may include additional or alternative clinical tools, are envisaged with respect to the needs of any specific procedure.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 struts refers to groups having 1, 2, or 3 struts. Similarly, a group having 1-5 struts refers to groups having 1, 2, 3, 4, or 5 struts, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

What is claimed is:

1. An embolic protection device, comprising:
    a) a scaffold, comprising:
        i) a proximal eyelet extending along an eyelet axis;
        ii) a frame adapted to operate between expanded and collapsed profiles, wherein the frame comprises:
            A) a proximal strut region comprising a plurality of proximal struts extending distally from the proximal eyelet;
            B) a frame-cell region having a frame-cell region length extending distally from a frame-cell region proximal edge to a frame cell region distal edge, wherein the frame-cell region proximal edge is continuous with the proximal strut region; and
            C) a distal strut region having a distal strut region length comprising a plurality of distal struts extending distally from the frame-cell region distal edge; and
        iii) a distal eyelet connected to the plurality of distal struts opposite the frame-cell region, the distal eyelet extending along the eyelet axis; and
    b) a conical filter, consisting of:
        i) an imperforate section extending distally from an imperforate section proximal edge spaced from an imperforate section distal portion, wherein the imperforate section proximal edge defines an ingress into the conical filter; and
        ii) a porous section configured for fluid flow therethrough, the porous section extending distally from the imperforate section distal portion to terminate at a porous section distal end, wherein the porous section distal end is not directly coupled to the distal eyelet, instead terminating proximal the distal eyelet, and wherein the porous section is spaced inwardly from the plurality of distal struts comprising the distal strut region of the frame,
    c) wherein the imperforate section of the conical filter is coupled to the frame-cell region proximal edge and extends at least part-way along the frame-cell region length toward the frame-cell distal edge, or the imperforate section is coupled to the frame-cell region distal edge and extends part-way along the distal strut region length, and
    d) wherein, other than the conical filter, the embolic protection device does not have another filter.

2. The embolic protection device of claim 1, wherein the distal strut region of the frame is continuous with a distal edge of the frame-cell region.

3. The embolic protection device of claim 1, wherein the frame is composed of a material selected from the group of nitinol, stainless steel, titanium, and alloys thereof, and combinations thereof.

4. The embolic protection device of claim 1, wherein the proximal and distal struts of the frame are radially oriented relative to the eyelet axis, and wherein the proximal and distal struts each extend from their respective proximal and distal eyelets at an angle ranging from about 10° to about 90° relative to the eyelet axis.

5. The embolic protection device of claim 1, wherein the imperforate and porous sections comprising the conical filter are each comprised of a polymeric material selected from the group of polytetrafluoroethylene (PTFE), ePTFE, polyurethane, polyethylene, polyethylene, polypropylene (PP), polyvinylchloride (PVC), polyamide (nylon), polyethylene tetraphlalate, polyether-ether ketone (PEEK), polyether block amide (PEBA), polytetrafluoroethylene (PTFE), and combinations thereof.

6. The embolic protection device of claim 1, wherein a perforated material comprising the porous section of the conical filter has perforations ranging in diameter from about 5 μm to about 200 μm.

7. The embolic protection device of claim 1, wherein the imperforate section of the conical filter is configured to circumferentially conform to an interior segment of the frame-cell region.

8. The embolic protection device of claim 7, wherein the imperforate section is composed of alternating embrasure segments, each embrasure segment separated by an abapical region disposed about the eyelet axis to define a coupling configuration.

9. The embolic protection device of claim 8, wherein at least one of the abapical regions is occupied by the imperforate material to define an off-set coupling configuration.

10. The embolic protection device of claim 1, wherein the distal struts comprising the distal strut region of the frame taper along the eyelet axis from the frame-cell region towards the distal eyelet.

11. The embolic protection device of claim 1, wherein an attachment couples the imperforate section comprising the conical filter to an interior segment of the frame-cell region.

12. The embolic protection device of claim 1, wherein the distal strut region length of the frame ranges from about 1.5 times to about 10 times that of either or both the proximal strut region and the frame-cell region.

13. The embolic protection device of claim 1, wherein the conical filter is disposed internal to the scaffold and tapers distally along the eyelet axis.

14. The embolic protection device of claim 1, wherein the imperforate section of the conical filter has an area ranging from 2 in$^2$ to 5 in$^2$.

15. The embolic protection device of claim 1, wherein the frame-cell region of the frame comprises a strut matrix circumferentially disposed about the eyelet axis.

16. The embolic protection device of claim 1, wherein, when the frame of the scaffold has an expanded profile, the embolic protection device is radially ridged to maintain blood vessel apposition.

17. The embolic protection device of claim 1, wherein the frame comprises three integral struts.

18. The embolic protection device of claim 1, wherein, when the scaffold has an expanded profile, the porous section distal end of the conical filter resides along the eyelet axis.

19. An embolic protection system, comprising:
  a) an embolic protection device, comprising:
    i) a scaffold, comprising:
      A) a proximal eyelet defining a proximal end of the scaffold;
      B) a distal eyelet defining a distal end of the scaffold, wherein the proximal and distal eyelets are aligned along a longitudinal eyelet axis; and
      C) a frame disposed between the proximal and distal eyelets, the frame comprising:
        A') proximal and distal struts extending distally and proximally from their respective proximal and distal eyelets to respectively define proximal and distal strut regions; and
        B') a frame-cell region disposed between and continuous with the proximal and distal strut regions, the frame-cell region having a frame-cell region length extending distally from a frame-cell region proximal edge to a frame-cell region distal edge, wherein the frame-cell region proximal edge extends distally from the proximal struts, and wherein the distal strut region has a distal strut region length comprising the distal struts extending distally from the frame-cell region distal edge;
    ii) a distally tapered filter, consisting of:
      A) an imperforate section extending distally from an imperforate section proximal edge spaced from an imperforate section distal portion, wherein the imperforate section proximal edge defines an ingress into the distally tapered filter; and
      B) a porous section configured for fluid flow therethrough, the porous section extending distally from the imperforate section distal portion to terminate at a porous section distal end, wherein the porous section distal end is not directly coupled to the distal eyelet, instead terminating proximal the distal eyelet, and wherein the porous section is spaced inwardly from the plurality of distal struts comprising the distal strut region,
      C) wherein the imperforate section of the distally tapered filter is coupled to the frame-cell region proximal edge and extends at least part-way along the frame-cell region length toward the frame-cell distal edge, or the imperforate section is coupled to the frame-cell region distal edge and extends part-way along the distal strut region length, and
      D) wherein, other than the distally tapered filter, the embolic protection device does not have another filter; and
  b) an insertable guide extending through the frame and the proximal and distal eyelets to facilitate deployment and directional positioning of the embolic protection device along the eyelet axis.

20. The embolic protection system of claim 19, wherein the frame of the scaffold of the embolic protection device is composed of a material selected from the group of nitinol, stainless steel, titanium, and alloys thereof, and combinations thereof.

21. The embolic protection system of claim 19, wherein the proximal and distal struts of the frame of the embolic protection device are radially oriented relative to the eyelet axis, and wherein the proximal and distal struts each extend from their respective proximal and distal eyelets at an angle ranging from about 10° to about 90° relative to the eyelet axis.

22. The embolic protection system of claim 19, wherein the imperforate and porous sections comprising the distally tapered filter of the embolic protection device are each comprised of a polymeric material selected from the group of ePTFE, polytetrafluoroethylene (PTFE), polyurethane, polyethylene, polyethylene, polypropylene (PP), polyvinylchloride (PVC), polyamide (nylon), polyethylene tetraphlalate, polyether-ether ketone (PEEK), polyether block amide (PEBA), polytetrafluoroethylene (PTFE), and combinations thereof.

23. The embolic protection system of claim 19, wherein a perforated material comprising the porous section of the distally tapered filter of the embolic protection device has perforations ranging in diameter from about 5 µm to about 200 µm.

24. The embolic protection system of claim 19, wherein the imperforate section of the distally tapered filter of the embolic protection device is composed of alternating embrasure segments, each embrasure segment separated by an abapical region disposed about the eyelet axis to define a coupling configuration.

25. The embolic protection system of claim 24, wherein at least one of the abapical regions is occupied by the imperforate material to define an off-set coupling configuration.

26. The embolic protection system of claim 19, wherein an attachment couples the imperforate section comprising the distally tapered filter of the embolic protection device to the frame-cell region.

27. The embolic protection system of claim 19, wherein the distal strut region length of the frame of the embolic protection device ranges from about 1.5 times to about 10 times that of either or both the proximal strut region and the frame-cell region.

28. The embolic protection system of claim 19, wherein the frame-cell region of the frame of the embolic protection device comprises a strut matrix circumferentially disposed about the eyelet axis.

29. The embolic protection system of claim 19, wherein, when the frame of the scaffold has an expanded profile, the embolic protection device is radially ridged to maintain blood vessel apposition.

30. The embolic protection system of claim 19, wherein the frame of the scaffold of the embolic protection device comprises three integral struts.

31. The embolic protection system of claim 19, wherein, when the scaffold has an expanded profile, the porous section distal end of the distally tapered filter of the embolic protection device resides along the eyelet axis.

32. A method for preventing a disease or condition associated with the presence of an embolism in a subject in need thereof, the method comprising the steps of:
 a) selecting a subject;
 b) accessing one or more blood vessels of the subject;
 c) unilaterally or bilaterally positioning an insertable guide into the one or more blood vessels of the subject;
 d) providing an embolic protection device, comprising:
  i) a scaffold, comprising:
   A) a proximal eyelet defining a proximal end of the scaffold, and a distal eyelet defining a distal end of the scaffold, wherein the proximal and distal eyelets are aligned along a longitudinal eyelet axis; and
   B) a frame disposed between the proximal and distal eyelets, the frame comprising proximal and distal struts extending distally and proximally from their respective proximal and distal eyelets to respectively define proximal and distal strut regions, and a frame-cell region disposed between and continuous with the proximal and distal strut regions, the frame-cell region having a frame-cell region length extending distally from a frame-cell region proximal edge to a frame-cell region distal edge, wherein the frame-cell region proximal edge extends distally from the proximal struts, and wherein the distal strut region has a distal strut region length comprising the distal struts extending distally from the frame-cell region distal edge; and
  ii) a conical filter, consisting of:
   A) an imperforate section extending distally from an imperforate section proximal edge spaced from an imperforate section distal portion, wherein the imperforate section proximal edge defines an ingress into the conical filter; and
   B) a porous section configured for fluid flow therethrough, the porous section extending distally from the imperforate section distal portion to terminate at a porous section distal end, wherein the porous section distal end is not directly coupled to the distal eyelet, instead terminating proximal the distal eyelet, and wherein the porous section is spaced inwardly from the plurality of distal struts comprising the distal strut region,
   C) wherein the imperforate section of the conical filter is coupled to the frame-cell region proximal edge and extends at least part-way along the frame-cell region length toward the frame-cell distal edge, or the imperforate section is coupled to the frame-cell region distal edge and extends part-way along the distal strut region length, and
   D) wherein, other than the conical filter, the embolic protection device does not have another filter;
 e) deploying the embolic protection device over the insertable guide so that the guide extends through the frame and the proximal and distal eyelets along the eyelet axis, wherein steps c) and e) are performed separately, sequentially or simultaneously;
 f) capturing embolic debris frcm the one or more blood vessels; and
 g) removing the embolic protection device with the captured debris from over the guide positioned in the subject's one or more blood vessels to help prevent the disease or condition associated with the embolism in the subject.

33. The embolic protection device of claim 1, wherein the porous section of the conical filter is not supported by the distal struts comprising the distal strut region of the frame.

34. The method of claim 32, wherein, with the scaffold having an expanded profile, the porous section distal end of the conical filter resides along the eyelet axis.

* * * * *